(12) United States Patent
Dymock et al.

(10) Patent No.: US 6,538,015 B1
(45) Date of Patent: Mar. 25, 2003

(54) ANTI-HIV PYRAZOLE DERIVATIVES

(75) Inventors: Brian William Dymock, St. Albans (GB); Adrian Liam Gill, Wilshamstead (GB); Philip Stephen Jones, Welwyn Garden City (GB); Kevin Edward Burdon Parkes, Letchworth (GB); Martin John Parratt, Hertford (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/154,585

(22) Filed: May 24, 2002

(30) Foreign Application Priority Data

Jun. 4, 2001 (GB) .............................................. 0113524

(51) Int. Cl.[7] ....................... A61K 31/415; A61P 31/18; C07D 231/18; C07D 401/06
(52) U.S. Cl. ....................... 514/407; 514/341; 544/333; 546/276.1; 548/365.7; 548/370.1; 548/370.4
(58) Field of Search ............................ 548/365.7, 370.1, 548/370.4; 546/276.1; 514/407

(56) References Cited

U.S. PATENT DOCUMENTS 5,786,302 A 7/1998 Mathews et al.
6,005,109 A 12/1999 Faraci et al.

FOREIGN PATENT DOCUMENTS

| EP | 627 423 | 7/1994 |
| EP | 0 786 455 | 7/1997 |
| WO | WO 02/04424 | 1/2002 |
| WO | WO 02/30907 | 4/2002 |

OTHER PUBLICATIONS

D. L. Comins et al., *Tetrahedron Letters*, vol. 27, pp. 1869–1872 (1986).
Pauwels et al., *J. Virology Methods*, vol. 20, pp. 309–321 (1988).
J. E. Lynch et al., *J. Org. Chem.*, vol. 62, pp. 9223–9228 (1997).
Genin M J et al, Journal of Medicinal Chemistry, American Chemical Society, vol. 43, pp. 1034–1040 (2000).

*Primary Examiner*—Robert W. Ramsuer
(74) *Attorney, Agent, or Firm*—George W. Johnston; Dennis P. Tramaloni

(57) ABSTRACT

The invention is concerned with novel pyrazole derivatives, a process for their manufacture, pharmaceutical compositions and the use of such compounds in medicine. In particular, the compounds of formula I are inhibitors of the human immunodeficiency virus reverse transcriptase enzyme which is involved in viral replication. Consequently the compounds of this invention may be advantageously used as therapeutic agents for HIV mediated process.

9 Claims, No Drawings

ANTI-HIV PYRAZOLE DERIVATIVES

BACKGROUND OF THE INVENTION

The disease Acquired Immunodeficiency Syndrome (AIDS) is the end result of infection by the distinct retroviruses, human immunodeficiency virus type-1 (HIV-1) or type-2 (HIV-2). Several critical points in the virus life cycle have been identified as possible targets for therapeutic intervention. Inhibition of one of these, the transcription of viral RNA to viral DNA (controlled by reverse transcriptase, RT), has provided a number of the current therapies used in treating AIDS. Inhibition of reverse transcriptase provided the first form of treatment for HIV infection with 3'-azido-3'-deoxythymidine (AZT). Since then several inhibitors have been launched, broadly forming two classes: nucleoside analogues and non-nucleosides. As an example of the latter it has been found that certain benzoxazinones, e.g. efavirenz, are useful in the inhibition of HIV RT. However, development of strains of the virus resistant to current RT inhibitors is a constant problem. Therefore, development of compounds effective against resistant strains is an important goal.

Pyrazole derivatives have been described in the literature with different uses (e.g. agrochemistry or treatment of stress-relating illness).

EP 0 627 423 describes pyrazole derivatives and their use as agrohorticultural bactericides.

U.S. Pat. No. 6,005,109 describes pyrazole derivatives and their use in the treatment of stress-relating illness.

U.S. Pat. No. 5,786,302 describes pyrazole derivatives and their use as herbicides.

SUMMARY OF THE INVENTION

The present invention provides pyrazole compounds of the general formula

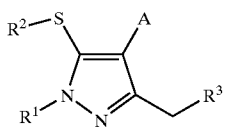

I which are potent inhibitors of the human immunodeficiency virus reverse transcriptase enzyme (HIV RT) which is involved in viral replication. Consequently the compounds of this invention can be advantageously used as therapeutic agents for the treatment of diseases mediated by the human immunodeficiency virus (HIV).

DETAILED DESCRIPTION OF THE INVENTION

This object can be achieved with compounds of formula I

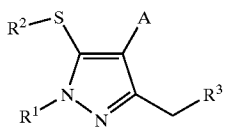

I wherein
   $R^1$ is alkyl or substituted alkyl;
   $R^2$ is aryl or substituted aryl;
   $R^3$ is hydroxy, amino, azido, hydroxy-$C_{1-4}$-alkyl, $C_{1-4}$-alkyl-sulfonyl-amino or a group of the formula —X—C(=O)—Z,
      wherein X represents NR"", O or a single bond;
         wherein R"" is hydrogen or $C_{1-4}$-alkyl, and
      wherein Z is $C_{1-4}$-alkyl, $C_{1-4}$-alkoxy or NR", R'";
         wherein R", R'" are independently of each other hydrogen or $C_{1-4}$-alkyl;
   A signifies alkyl, substituted alkyl, aryl-methyl, substituted aryl-methyl, aryl-methoxy-methyl, substituted aryl-methoxy-methyl, heterocyclyl-methyl, substituted heterocyclyl-methyl, heterocyclyl-methoxy-methyl or substituted heterocyclyl-methoxy-methyl;
with ethers of compounds of formula I as well as with pharmaceutically acceptable salts of the foregoing.

The term "alkyl" as used herein, and if not specified by the number of carbon atoms, denotes an optionally substituted straight or branched chain hydrocarbon residue containing 1 to 12 carbon atoms, such as methyl, ethyl, n-propyl, isopropyl, n-butyl, sec-butyl, isobutyl, tert.-butyl, pentyl, hexyl, heptyl, octyl, nonyl, decyl, undecyl, dodecyl including their different isomers. The term "$C_{1-12}$-alkyl" denotes a straight or branched chain hydrocarbon residue containing 1 to 12 carbon atoms as defined above. The term "$C_{1-7}$-alkyl" denotes a straight or branched chain hydrocarbon residue containing 1 to 7 carbon atoms. The term "$C_{1-4}$-alkyl" denotes a straight or branched chain hydrocarbon residue containing 1 to 4 carbon atoms. Suitable substituents for the alkyl group are 1–6 fluorine substituents or 1–3 hydroxy substituents, preferably 1–3 fluorine substituents or 1–2 hydroxy substituents and most preferably 3 fluorine substituents or 1 hydroxy substituent. In case more than one substituent is attached to the alkyl group, these substituents can be identical or different from each other. Alkyl in $R^1$ is preferably a straight or branched chain hydrocarbon residue containing 1 to 12 carbon atoms as defined above. More preferably the alkyl group in $R^1$ is a straight or branched chain hydrocarbon residue containing 1 to 7 carbon atoms. In another preferred embodiment alkyl in $R^1$ is methyl, ethyl, propyl, isopropyl, n-butyl, sec-butyl, isobutyl or tert.-butyl. Most preferred alkyl in $R^1$ is isopropyl.

Substituted alkyl for $R^1$ is preferably a straight or branched chain hydrocarbon residue containing 1 to 12 carbon atoms as defined above substituted with 1–6 fluorine substituents, most preferably the trifluoromethyl group.

Alkyl for the substituent A is preferably a straight or branched chain hydrocarbon residue containing 1 to 12 carbon atoms as defined above. More preferred alkyl groups in $R^1$ are straight or branched chain hydrocarbon residues containing 1 to 7 carbon atoms. Most preferred alkyl in $R^1$ is methyl, ethyl, propyl, isopropyl, n-butyl, sec-butyl, isobutyl or tert.-butyl.

Substituted alkyl for the substituent A is preferably a straight or branched chain hydrocarbon residue containing 1 to 12 carbon atoms as defined above substituted with 1–3 hydroxy groups, most preferably the hydroxy-methyl group.

The term "hydroxy-$C_{1-4}$-alkyl" as used herein denotes a $C_{1-4}$-alkyl, preferably a $C_{1-2}$-alkyl as defined above which is substituted with a hydroxy group. Examples are hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl.

The term "$C_{1-4}$-alkyl-sulfonyl-amino" as used herein for the substituent $R^3$ denotes for example a methanesulfonamide, ethanesulfonamide, propanesulfonamide or butanesulfonamide. The NH-function of $C_{1-4}$-alkylsulfonyl-amino can as well be alkylated with $C_{1-4}$-alkyl as defined above, preferably methyl or ethyl.

The term "alkoxy" as used herein, denotes a straight or branched chain alkyl-oxy group wherein the "alkyl" portion is as defined above such as methoxy, ethoxy, n-propyloxy, isopropyloxy, n-butyloxy, isobutyloxy, tert.-butyloxy. More preferred alkoxy groups within the invention are methoxy or ethoxy.

Formula "—X—C(=O)—Z" as used herein denotes a chemical group wherein X represents NR'''', O or a single bond (wherein R'''' is hydrogen or $C_{1-4}$-alkyl); and wherein Z is $C_{1-4}$-alkyl, $C_{1-4}$-alkoxy or NR''R''' (wherein R', R''' are independently of each other hydrogen or $C_{1-4}$-alkyl). Preferably, the formula "—X—C(=O)—Z" as used herein denotes a chemical group wherein X represents NR'''' or O (wherein R'''' is hydrogen or $C_{1-4}$-alkyl); and wherein Z is $C_{1-4}$-alkyl, $C_{1-4}$-alkoxy or NR''R''' (wherein R'', R''' are independently of each other hydrogen or $C_{1-4}$-alkyl). More preferred, the formula "—X—C(=O)—Z" as used herein denotes a chemical group wherein X represents NR'''' or O (wherein R'''' is hydrogen or $C_{1-4}$-alkyl); and wherein Z is NR''R''' (wherein R'', R''' are independently of each other hydrogen or $C_{1-4}$-alkyl). Most preferred, the formula "—X—C(=O)—Z" as used herein denotes a chemical group wherein X represents O (wherein R'''' is hydrogen or $C_{1-4}$-alkyl); and wherein Z is NR''R''' (wherein R'', R''' are independently of each other hydrogen or $C_{1-4}$-alkyl). Examples of the chemical group of formula "—X—C(=O)—Z" are amino-carbonyl-oxy, methyl-amino-carbonyl-oxy, di-methyl-amino-carbonyl-oxy, amino-carbonyl-amino, methyl-amino-carbonyl-amino, di-methyl-amino-carbonyl-amino, amino-carbonyl-(methyl)-amino, methyl-amino-carbonyl-(methyl)-amino, di-methyl-amino-carbonyl-(methyl)-amino, methoxy-carbonyl-amino, methoxy-carbonyl-(methyl)-amino, ethoxy-carbonyl-amino or ethoxy-carbonyl-(methyl)-amino.

The term "aryl" as used herein denotes an optionally substituted phenyl and naphthyl, both optionally benz-fused to an optionally substituted saturated, partially unsaturated or aromatic monocyclic, bicyclic or tricyclic heterocycle or carbocycle e.g. to cyclohexyl or cyclopentyl. Preferably the term "aryl" as used herein denotes an optionally substituted phenyl group.

Suitable substituents for aryl (preferably phenyl) can be selected from 1–5 substituents selected from $C_{1-4}$-alkyl, substituted $C_{1-4}$-alkyl, $C_{1-4}$-alkoxy, $C_{1-4}$-alkylthio, fluorine, chlorine, bromine and cyano; wherein substituted $C_{1-4}$-alkyl means $C_{1-4}$-alkyl substituted with 1–3 substituents selected from hydroxy, $C_{1-4}$-alkoxy, CONH$_2$, NRR' and wherein R and R' are independently of each other hydrogen, $C_{1-4}$-alkyl or —C(=O)CH$_3$.

In case more than one substituent is attached to the aryl group, these substituents can be identical or different from each other.

Aryl in $R^2$ is preferably an unsubstituted or substituted phenyl or naphthyl (preferably phenyl) with suitable substituents selected from 1 to 5 substituents, preferably 1–4 substituents, more preferably 1–3 substituents selected from $C_{1-4}$-alkyl (preferably $C_{1-2}$-alkyl), substituted $C_{1-4}$-alkyl (preferably substituted $C_{1-2}$-alkyl), $C_{1-4}$-alkoxy (preferably $C_{1-2}$-alkoxy), $C_{1-4}$-alkylthio (preferably $C_{1-2}$-alkylthio), fluorine, chlorine, bromine and cyano; wherein substituted $C_{1-4}$-alkyl (preferably substituted $C_{1-2}$-alkyl) means $C_{1-4}$-alkyl (preferably $C_{1-2}$-alkyl) substituted with 1–3 substituents (preferably 1–2 substituents, more preferred 1 substituent) selected from hydroxy, $C_{1-4}$-alkoxy (preferably $C_{1-2}$-alkoxy), CONH$_2$ and NRR'; and wherein R and R' are independently of each other hydrogen, $C_{1-4}$-alkyl (preferably $C_{1-2}$-alkyl) or —C(=O)CH$_3$. In case more than one substituent is attached to the aryl group, these substituents can be identical or different from each other. Preferred substituents for the phenyl group are 1–5 substituents (more preferred 1–3 substituents) selected from $C_{1-4}$-alkyl, $C_{1-4}$-alkoxy, $C_{1-4}$-alkylthio, fluorine, chlorine, bromine and cyano (more preferred fluorine, chlorine, bromine and cyano). Most preferred substituents for the phenyl group are 1–5 substituents (more preferred 1–3 substituents) selected from chlorine and cyano. Examples of substituted aryl groups are 2-methyl-phenyl, 3-methyl-phenyl, 4-methyl-phenyl, 2-ethyl-phenyl, 3-ethyl-phenyl, 4-ethyl-phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,6-dimethylphenyl, 2,4,6-trimethylphenyl, 3,4,5-trimethylphenyl, 2,3,4-trimethylphenyl, 2,4,5-trimethylphenyl, 2-methoxy-phenyl, 3-methoxy-phenyl, 4-methoxy-phenyl, 2,3-dimethoxy-phenyl, 2,4-dimethoxy-phenyl, 2,5-dimethoxy-phenyl, 2,6-dimethoxy-phenyl, 3,4-dimethoxy-phenyl, 3,5-dimethoxy-phenyl, 3,6-dimethoxy-phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 3,6-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3,6-dichlorophenyl, 2,4,6-trichlorophenyl, 3,4,5-trichlorophenyl, 2,3,4-trichlorophenyl, 2,4,5-trichlorophenyl, 2-bromophenyl, 3-bromophenyl, 4-bromophenyl, 2,3-dibromophenyl, 2,4-dibromophenyl, 2,5-dibromophenyl, 2,6-dibromophenyl, 3,4-dibromophenyl, 3,5-dibromophenyl, 3,6-dibromophenyl, 2-cyano-phenyl, 3-cyano-phenyl, 4-cyano-phenyl, 2,3-di-cyano-phenyl, 2,4-di-cyano-phenyl, 2,5-di-cyano-phenyl, 2,6-di-cyano-phenyl, 3,4-di-cyano-phenyl, 3,5-di-cyano-phenyl, 3,6-di-cyano-phenyl, 2-(hydroxymethyl)phenyl, 3-(hydroxymethyl)phenyl, 4-(hydroxymethyl)phenyl, 2-chloro-4-fluorophenyl, 2-chloro-6-methyl-phenyl, 3-chloro-5-bromo-phenyl, 3-chloro-5-propyl-phenyl, 3-chloro-5-methyl-phenyl, 3-chloro-5-ethyl-phenyl, 3-chloro-5-(hydroxymethyl)-phenyl, 3-chloro-5-cyano-phenyl, 3-chloro-5-(1,2-propanediol)-phenyl or 2-naphthyl. Preferred example for aryl in $R^2$ is 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3,6-dichlorophenyl, 2,4,6-trichlorophenyl, 3,4,5-trichlorophenyl, 2,3,4-trichlorophenyl, 2,4,5-trichlorophenyl. More preferred example for aryl in $R^2$ is 3,5-dichlorophenyl.

Aryl in aryl-methyl for the substituent A is as defined above, preferably phenyl.

Substituted aryl in substituted aryl-methyl for the substituent A is as defined above, with suitable substituents selected from 1 to 5 substituents, preferably 1–4 substituents, more preferably 1–3 substituents selected from $C_{1-4}$-alkoxy (preferably $C_{1-2}$-alkyl), fluorine, chlorine and bromine. In case more than one substituent is attached to the aryl group, these substituents can be identical or different from each other. Examples for substituted aryl in substituted aryl-methyl are preferably 2-methoxy-phenyl, 3-methoxy-phenyl, 4-methoxy-phenyl, 2,3-dimethoxy-phenyl, 2,4-dimethoxy-phenyl, 2,5-dimethoxy-phenyl, 2,6-dimethoxy-phenyl, 3,4-dimethoxy-phenyl, 3,5-dimethoxy-phenyl, 3,6-dimethoxy-phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl or 3,6-difluorophenyl.

Aryl in aryl-methoxy-methyl for the substituent A is as defined above, preferably phenyl.

Substituted aryl in substituted aryl-methoxy-methyl, for the substituent A is as defined above, with suitable substituents selected from 1 to 5 substituents, preferably 1–4 substituents, more preferably 1–3 substituents selected from $C_{1-4}$-alkyl, $C_{1-4}$-alkoxy, $C_{1-4}$-alkylthio, $C_{1-4}$-alkylamino, hydroxy, cyano, amino, mercapto groups, fluorine, chlorine and bromine. In case more than one substituent is attached to the aryl group, these substituents can be identical or different from each other. Examples for substituted aryl in substituted substituted aryl-methoxy-methyl are 2-methoxyphenyl, 3-methoxy-phenyl, 4-methoxy-phenyl, 2,3-dimethoxy-phenyl, 2,4-dimethoxy-phenyl, 2,5-dimethoxy-phenyl, 2,6-dimethoxy-phenyl, 3,4-dimethoxy-phenyl, 3,5-dimethoxy-phenyl, 3,6-dimethoxy-phenyl, 2-cyanophenyl, 3-cyanophenyl, 4-cyanophenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl or 3,6-difluorophenyl.

The term "heterocyclyl" as used herein denotes an aromatic or non-aromatic monocyclic or bicyclic heterocyclic system which contains 1, 2, 3 or 4 hetero atoms, preferably 1, 2 or 3 hetero atoms, with the hetero atoms being selected from nitrogen, oxygen and sulfur. Examples of heterocyclyl are 2-furyl, 3-furyl, 1-pyrrolyl, 2-pyrrolyl, 2-pyridyl, 3-pyridyl, 4-pyridyl, 1-indolyl, 2-indolyl or 3-indolyl, pyridazin-3-yl, pyridazin-4-yl, 2-thienyl, 3-thienyl, [1,3,4]thiadiazol-2-yl, [1,3,4]thiadiazol-5-yl, tetrahydro-pyran-4-yl, piperidin-2-yl, piperidin-3-yl, piperidin-4-yl, 1H-imidazol-2-yl, 1H-imidazol-4-yl, 1H-imidazol-5-yl, pyrrolidin-1-yl, pyrrolidin-2-yl, pyrrolidin-3-yl, pyrrolidin-4-yl, pyrrolidin-5-yl, pyrimidin-2-yl, pyrimidin-4-yl, pyrimidin-5-yl or pyrimidin-6-yl.

Suitable substituents for heterocyclyl can be selected from 1,2,3 or 4 (where chemically possible), preferably 1 or 2, selected from $C_{1-4}$-alkyl (preferably $C_{1-2}$-alkyl), $C_{1-4}$-alkoxy (preferably $C_{1-2}$-alkoxy), $C_{1-4}$-alkylthio (preferably $Cl_{1-2}$-alkylthio), $Cl_{1-4}$-alkylamino (preferably $C_{1-2}$-alkylamino), hydroxy, cyano, amino, mercapto groups, fluorine, chlorine and bromine.

In case more than one substituent is attached to the aryl group, these substituents can be identical or different from each other.

Heterocyclyl in heterocyclyl-methyl or heterocyclyl-methoxy-methyl for the substituent A is as defined above, preferably 1-furyl, 2-furyl, 1-pyrrolyl, 2-pyrrolyl, 1-thiophenyl, 2-thiophenyl, 2-pyridyl, 3-pyridyl or 4-pyridyl, more preferred 2-pyridyl, 3-pyridyl, 4-pyridyl, pyrimidin-2-yl, pyrimidin-4-yl, pyrimidin-5-yl or pyrimidin-6-yl. Preferred heterocyclyl in heterocyclyl-methyl or heterocyclyl-methoxy-methyl is pyridyl, most preferred 4-pyridyl.

Substituted heterocyclyl in substituted heterocyclyl-methyl or substituted heterocyclyl-methoxy-methyl for the substituent A are as defined above. Suitable substituents for heterocyclyl are selected from 1, 2, 3 or 4 substituents, preferably 1, 2 or 3 substituents, more preferably 1 or 2 substituents, and most preferably 1 substituent, wherein these substituents are selected from $C_{1-4}$-alkyl (preferably $C_{1-2}$-alkyl), $C_{1-4}$-alkoxy (preferably $C_{1-2}$-alkoxy), $C_{1-4}$-alkylthio (preferably $C_{1-2}$-alkylthio), $C_{1-4}$-alkylamino (preferably $C_{1-2}$-alkylamino), hydroxy, cyano, amino, mercapto groups, fluorine, chlorine and bromine. Preferred substituents for heterocyclyl are selected from 1, 2, 3 or 4 substituents, preferably 1, 2 or 3 substituents, more preferably 1 or 2 substituents, and most preferably 1 substituent, wherein these substituents are selected from 1–4 substituents selected from $C_{1-4}$-alkyl, fluorine, chlorine and bromine. More preferred substituents for heterocyclyl are selected from 1, 2, 3 or 4 substituents, preferably 1, 2 or 3 substituents, more preferably 1 or 2 substituents, and most preferably 1 substituent, wherein these substituents are selected from $C_{1-4}$-alkyl and bromine. Examples for substituted heterocyclyl are 2-methyl-pyridyl, 3-methyl-pyridyl, 4-methyl-pyridyl, 2,3-dimethylpyridyl, 2,4-dimethylpyridyl, 2,5-dimethylpyridyl, 2,6-dimethylpyridyl, 3,4-dimethylpyridyl, 3,5-dimethylpyridyl, 3,6-dimethylpyridyl, 2-methoxy-pyridyl, 3-methoxy-pyridyl, 4-methoxy-pyridyl, 2,3-dimethoxy-pyridyl, 2,4-dimethoxy-pyridyl, 2,5-dimethoxy-pyridyl, 2,6-dimethoxy-pyridyl, 3,4-dimethoxy-pyridyl, 3,5-dimethoxy-pyridyl, 3,6-dimethoxy-pyridyl, 2-fluoro-pyridyl, 3-fluoro-pyridyl, 4-fluoro-pyridyl, 2,3-difluoro-pyridyl, 2,4-difluoro-pyridyl, 2,5-difluoro-pyridyl, 2,6-difluoro-pyridyl, 3,4-difluoro-pyridyl, 3,5-difluoro-pyridyl, 3,6-difluoro-pyridyl, 2-chloro-pyridyl, 3-chloro-pyridyl, 4-chloro-pyridyl, 2,3-dichloro-pyridyl, 2,4-dichloro-pyridyl, 2,5-dichloro-pyridyl, 2,6-dichloro-pyridyl, 3,4-dichloro-pyridyl, 3,5-dichloro-pyridyl, 3,6-dichloro-pyridyl, 2-bromo-pyridyl, 3-bromo-pyridyl, 4-bromo-pyridyl, 2,3-dibromo-pyridyl, 2,4-dibromo-pyridyl, 2,5-dibromo-pyridyl, 2,6-dibromo-pyridyl, 3,4-dibromo-pyridyl, 3,5-dibromo-pyridyl, 3,6-dibromo-pyridyl, 5-bromo-2-methyl-pyrimidin-4-yl, 2-bromo-5-methyl-pyrimidin-4-yl, 5-bromo-6-methyl-pyrimidin-4-yl, 6-bromo-2-methyl-pyrimidin-4-yl, 6-bromo-5-methyl-pyrimidin-4-yl, 5-bromo-pyrimidin-4-yl, 5-methyl-pyrimidin-4-yl, 2-bromo-pyrimidin-4-yl, 2-methyl-pyrimidin-4-yl, 6-bromo-pyrimidin-4-yl or 6-methyl-pyrimidin-4-yl. For all the cited examples for "substituted heterocyclyl" these substituents can be at any chemically possible position. For example methylpyridyl means that the methyl substituent may be attached in the 3, 4, 5 or 6 position of a 2-pyridyl or in the 2,4,5 or 6 position of a 3-pyridyl or in the 2, 3, 5 or 6 position of a 4-pyridyl.

Any functional (i.e. reactive) group present in a side-chain may be protected, with the protecting group being a group which is known per se, for example, as described in "Protective Groups in Organic Synthesis", 2nd Ed., T. W. Greene and P. G. M. Wuts, John Wiley & Sons, New York, N.Y., 1991. For example, an amino group can be protected by tert.-butoxycarbonyl (BOC) or benzyloxycarbonyl (Z).

Compounds of formula I which are acidic can form pharmaceutically acceptable salts with bases such as alkali metal hydroxides, e.g. sodium hydroxide and potassium hydroxide; alkaline earth metal hydroxides, e.g. calcium hydroxide, barium hydroxide and magnesium hydroxide, and the like; with organic bases e.g. N-ethyl piperidine, dibenzylamine, and the like. Those compounds of formula (I) which are basic can form pharmaceutically acceptable salts with inorganic acids, e.g. with hydrohalic acids such as hydrochloric acid and hydrobromic acid, sulphuric acid, nitric acid and phosphoric acid, and the like, and with organic acids, e.g. with acetic acid, tartaric acid, succinic acid, fumaric acid, maleic acid, malic acid, salicylic acid, citric acid, methanesulphonic acid and p-toluene sulphonic acid, and the like. The formation and isolation of such salts can be carried out according to methods known in the art.

Preferred embodiments of the invention are novel compounds of formula I wherein $R^1$ is $C_{1-12}$-alkyl or $C_{1-12}$-alkyl substituted with 1–6 fluorines,
preferably wherein
$R^1$ is $C_{1-12}$-alkyl,
more preferred wherein
$R^1$ is $C_{1-7}$-alkyl,
most preferred wherein
$R^1$ is $C_{1-4}$-alkyl;

$R^2$ is aryl or substituted aryl,
wherein substituted aryl means aryl substituted with 1–5 substituents selected from $C_{1-4}$-alkyl, substituted $C_{1-4}$-alkyl, $C_{1-4}$-alkoxy, $C_{1-4}$-alkylthio, fluorine, chlorine, bromine and cyano; and wherein substituted $C_{1-4}$-alkyl means $C_{1-4}$-alkyl substituted with 1–3 substituents selected from hydroxy, $C_{1-4}$-alkoxy, $CONH_2$ and NRR',
wherein R and R' are independently of each other hydrogen, $C_{1-4}$-alkyl or —C(=O)CH$_3$,
preferably wherein
$R^2$ is phenyl or substituted phenyl,
wherein substituted phenyl means phenyl substituted with 1–5 substituents selected from $C_{1-4}$-alkyl, $C_{1-4}$-alkoxy, $C_{1-4}$-alkylthio, fluorine, chlorine, bromine and cyano,
more preferred wherein
$R^2$ is substituted phenyl,
wherein substituted phenyl means phenyl substituted with 1–5 substituents selected from fluorine, chlorine, bromine and cyano,
most preferred wherein
$R^2$ is substituted phenyl,
wherein substituted phenyl means phenyl substituted with 1–3 substituents selected from fluorine, chlorine, bromine and cyano;

$R^3$ is hydroxy, amino, azido, hydroxy-$C_{1-4}$-alkyl, $C_{1-4}$-alkyl-sulfonyl-amino or a group of the formula —X—C(=O)—Z,
wherein X represents NR"", O or a single bond; wherein R"" is hydrogen or $C_{1-4}$-alkyl, and
wherein Z is $C_{1-4}$-alkyl, $C_{1-4}$-alkoxy or NR"R'";
wherein R", R'" are independently of each other hydrogen or $C_{1-4}$-alkyl,
preferably wherein
$R^3$ is hydroxy, amino, azido, $C_{1-4}$-alkyl-sulfonyl-amino or a group of the formula —X—C(=O)—Z,
wherein X represents NR"" or O; wherein R"" is hydrogen or $C_{1-4}$-alkyl, and
wherein Z is $C_{1-4}$-alkyl, $C_{1-4}$-alkoxy or NR"R'"; wherein R", R'" are independently of each other hydrogen or $C_{1-4}$-alkyl,
more preferred wherein
$R^3$ is hydroxy or a group of the formula —X—C(=O)—Z,
wherein X represents NR"" or O; wherein R"" is hydrogen or $C_{1-4}$-alkyl, and
wherein Z is NR"R'"; wherein R"R'" are independently of each other hydrogen or $C_{1-4}$-alkyl,
most preferred wherein
$R^3$ is a group of the formula —X—C(=O)—Z,
wherein X represents NR"" or O; wherein R"" is hydrogen or $C_{1-4}$-alkyl, and
wherein Z is NR"R'"; wherein R", R'" are independently of each other hydrogen or $C_{1-4}$-alkyl;

A signifies $C_{1-12}$-alkyl, hydroxy-methyl, aryl-methyl, substituted aryl-methyl, aryl-methoxy-methyl, substituted aryl-methoxy-methyl, heterocyclyl-methyl, substituted heterocyclyl-methyl, heterocyclyl-methoxy-methyl or substituted heterocyclyl-methoxy-methyl,
wherein substituted aryl-methyl means aryl substituted with 1–5 substituents selected from $C_{1-4}$-alkoxy, fluorine, chlorine and bromine, and
wherein substituted aryl-methoxy-methyl means aryl substituted with 1–5 substituents, substituted heterocyclyl-methyl or substituted heterocyclyl-methoxy-methyl means heterocyclyl substituted with 1–4 substituents, the substituents selected from $C_{1-4}$-alkyl, $C_{1-4}$-alkoxy, $C_{1-4}$-alkylthio, $C_{1-4}$-alkylamino, hydroxy, cyano, amino, mercapto, fluorine, chlorine and bromine,
preferably wherein
A signifies heterocyclyl-methyl, substituted heterocyclyl-methyl or heterocyclyl-methoxy-methyl,
wherein substituted heterocyclyl-methyl means heterocyclyl substituted with 1–4 substituents selected from $C_{1-4}$-alkyl, fluorine, chlorine and bromine,
more preferred wherein
A signifies heterocyclyl-methyl, substituted heterocyclyl-methyl or heterocyclyl-methoxy-methyl,
wherein substituted heterocyclyl-methyl means heterocyclyl substituted with 1–2 substituents selected from $C_{1-4}$-alkyl and bromine,
most preferred wherein
A signifies heterocyclyl-methyl;

with ethers of compounds of formula I as well as with pharmaceutically acceptable salts of the foregoing.

A further preferred embodiment of the invention are novel compounds of formula I wherein $R^1$ is iso-propyl;

$R^2$ is substituted phenyl,
wherein substituted phenyl means phenyl substituted with 1–3 substituents selected from chlorine and cyano;

$R^3$ is a group of the formula —X—C(=O)—Z,
wherein X represents O, and
wherein Z is NR"R'"; wherein R", R'" are independently of each other hydrogen or $C_{1-4}$-alkyl;

A signifies pyridyl-methyl;

with ethers of compounds of formula I as well as with pharmaceutically acceptable salts of the foregoing.

Specific embodiments of the present invention are compounds of formula I listed in table 1, as well as their ethers and pharmaceutically acceptable salts thereof:

TABLE 1

| Structure | Systematic Name |
|---|---|
| 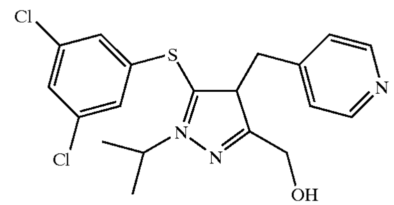 | 5-(3,5-Dichlorophenylthio)-1-isopropyl-4-[(4-pyridyl)methyl]-1H-pyrazole-3-methanol |
| 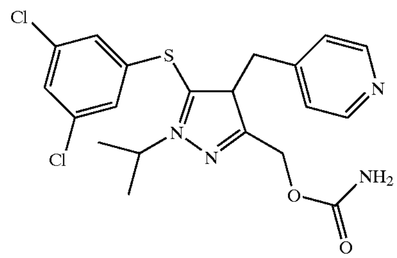 | Carbamic acid [5-(3,5-dichlorophenylthio)-1-isopropyl-4-[(4-pyridyl)methyl-1H-pyrazol-3-yl]methyl ester |
| 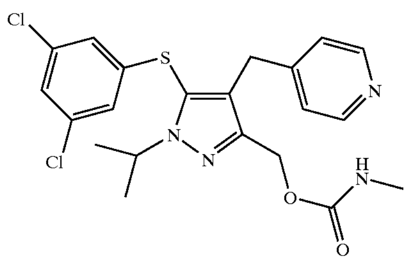 | Methylcarbamic acid [5-(3,5-dichlorophenylthio)-1-isopropyl-4-[(4-pyridyl)methyl]-1H-pyrazol-3-yl]methyl ester |
| 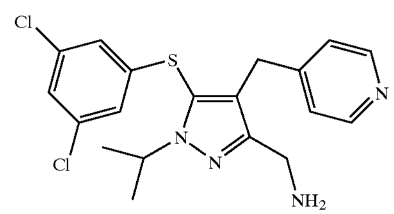 | 5-(3,5-Dichlorophenylthio)-1-isopropyl-4-[(4-pyridyl)methyl]-1H-pyrazole-3-methylamine |
| 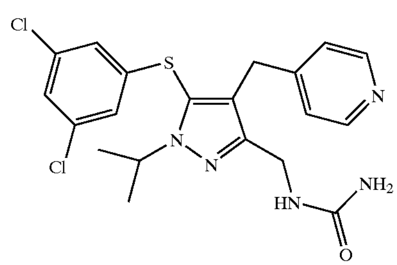 | 1-[[5-(3,5-Dichlorophenylthio)-1-isopropyl-4-[(4-pyridyl)methyl]-1H-pyrazol-3-yl]methyl]urea |
| 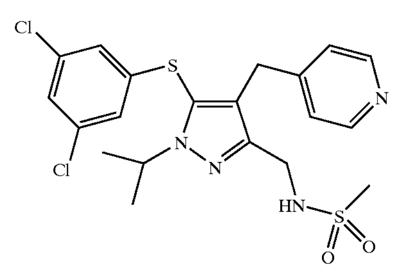 | N-[[5-(3,5-Dichlorophenylthio)-1-isopropyl-4-[(4-pyridyl)methyl]-1H-pyrazol-3-yl]methyl]methanesulfonamide |

TABLE 1-continued

| Structure | Systematic Name |
|---|---|
| 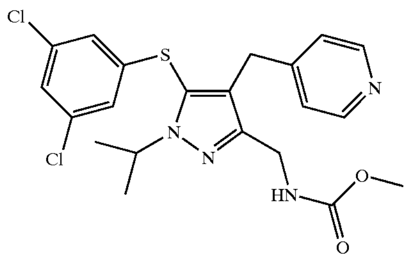 | Methyl [[5-(3,5-dichlorophenylthio)-1-isopropyl-4-[(4-pyridyl)methyl]-1H-pyrazol-3-yl]methyl]carbamate |
| 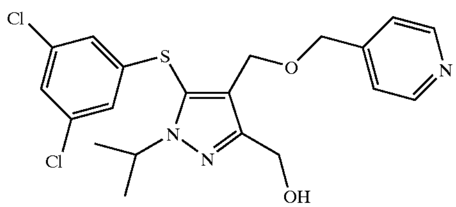 | 5-(3,5-Dichlorophenylthio)-1-isopropyl-4-[(4-pyridyl)methoxymethyl]-1H-pyrazole-3-methanol |
| 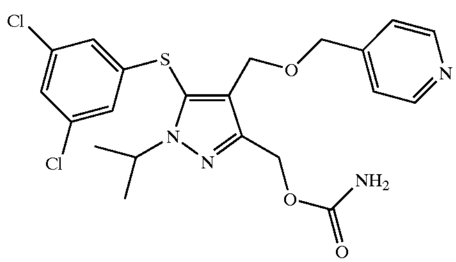 | Carbamic acid [5-(3,5-dichlorophenylthio)-1-isopropyl-4-[(4-pyridyl)methoxymethyl]-1H-pyrazol-3-yl]methyl ester |
| 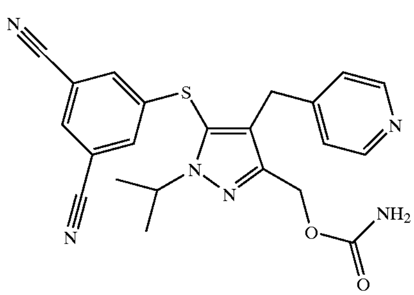 | Carbamic acid [5-(3,5-dicyanophenylthio)-1-isopropyl-4-[(4-pyridyl)methyl]-1H-pyrazol-3-yl]methyl ester |
| 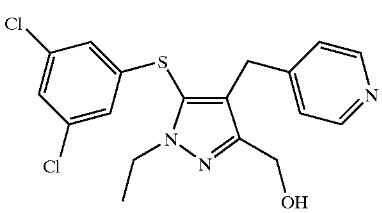 | 5-(3,5-Dichlorophenylthio)-1-ethyl-4-[(4-pyridyl)methyl]-1H-pyrazole-3-methanol |
| 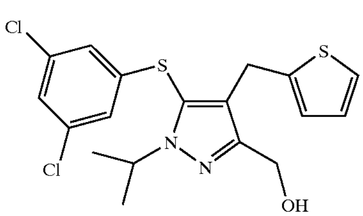 | 5-(3,5-Dichlorophenylthio)-1-isopropyl-4-(2-thenyl)-1H-pyrazole-3-methanol |

TABLE 1-continued

| Structure | Systematic Name |
|---|---|
| 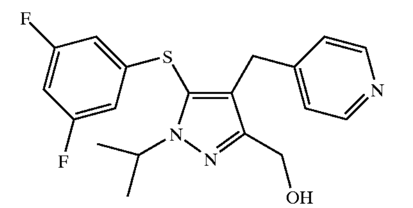 | 5-(3,5-Difluorophenylthio)-1-isopropyl-4-[(4-pyridyl)methyl]-1H-pyrazole-3-methanol |
| 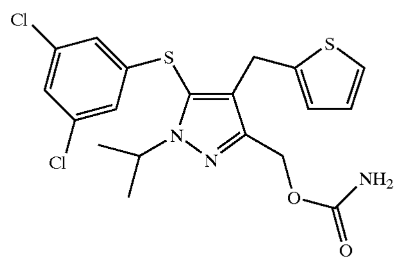 | Carbamic acid [5-(3,5-dichlorophenylthio)-1-isopropyl-4-(2-thenyl)-1H-pyrazol-3-yl]methyl ester |
| 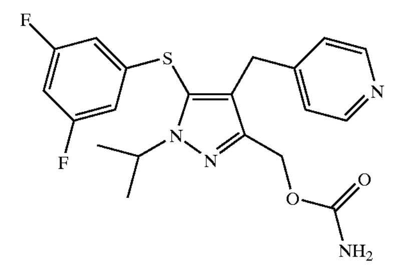 | Carbamic acid [5-(3,5-difluorophenylthio)-1-isopropyl-4-[(4-pyridyl)methyl]-1H-pyrazol-3-yl]methyl ester |
| 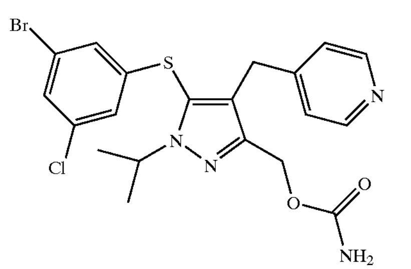 | 5-(3-Bromo-5-chlorophenylthio)-1-isopropyl-4-[(4-pyridyl)methyl]-1H-pyrazole-3-methanol |
| 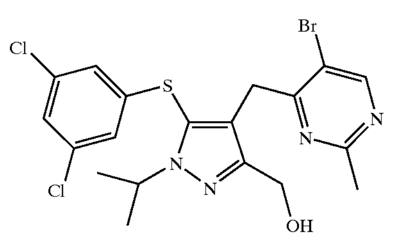 | 4-[(5-Bromo-2-methyl-4-pyrimidinyl)methyl]-5-(3,5-dichlorophenylthio)-1-isopropyl-1H-pyrazole-3-methanol |
| 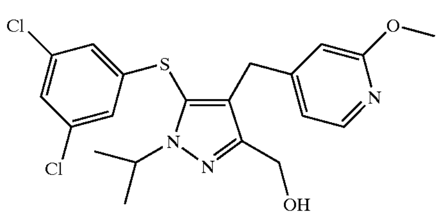 | 5-(3,5-Dichlorophenylthio)-1-isopropyl-4-(3-methoxybenzyl)-1H-pyrazole-3-methanol |

TABLE 1-continued

| Structure | Systematic Name |
| --- | --- |
| 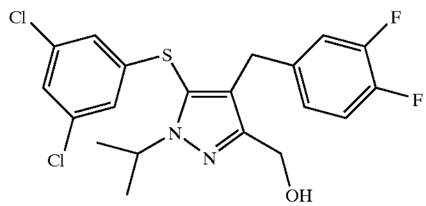 | 5-(3,5-Dichlorophenylthio)-4-(3,4-difluorobenzyl)-1-isopropyl-1H-pyrazole-3-methanol |
| 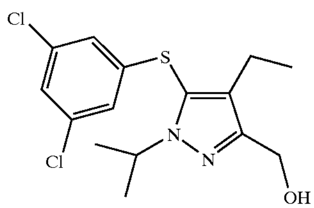 | 5-(3,5-Dichlorophenylthio)-4-ethyl-1-isopropyl-1H-pyrazole-3-methanol |
| 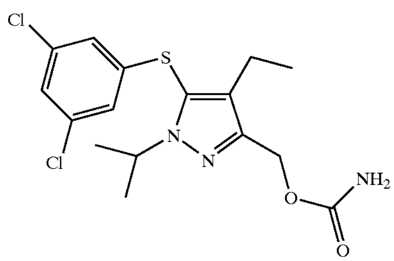 | Carbamic acid [5-(3,5-dichlorophenylthio)-4-ethyl-1-isopropyl-1H-pyrazol-3-yl]methyl ester |
| 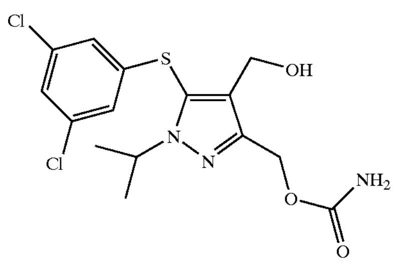 | Carbamic acid [5-(3)5-dichlorophenylthio)-4-(hydroxymethyl)-1-isopropyl-1H-pyrazol-3-yl]methyl ester |
| 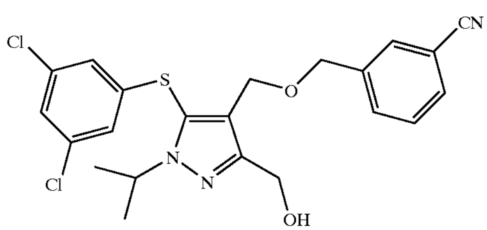 | 3-[[5-(3,5-Dichlorophenylthio)-3-(hydroxymethyl)-1-isopropyl-1H-pyrazol-4-yl]methoxymethyl]benzonitrile |
| 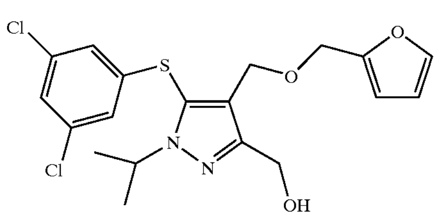 | 5-(3)5-Dichlorophenylthio)-4-[(2-furfuryloxy)methyl]-isopropyl-1H-pyrazole-3-methanol |

TABLE 1-continued

| Structure | Systematic Name |
|---|---|
| 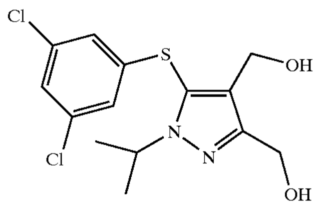 | 5-(3,5-Dichlorophenylthio)-1-isopropyl-1H-pyrazole-3,4-dimethanol |
| 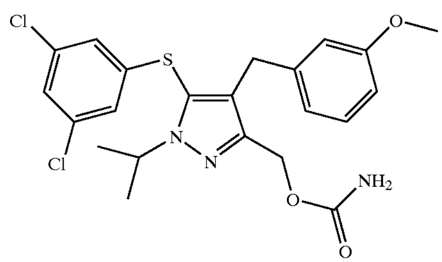 | Carbamic acid [5-(3,5-dichlorophenylthio)-1-isopropyl-4-(3-methoxybenzyl)-1H-pyrazol-3-yl]methyl ester |
| 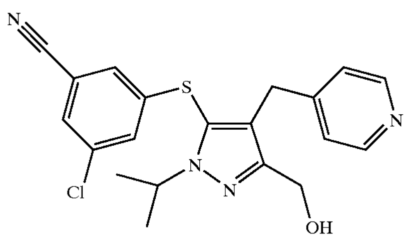 | 3-Chloro-5-[5-(hydroxymethyl)-2-isopropyl-4-[(4-pyridyl)methyl]-2H-pyrazol-3-ylthio]benzonitrile |
| 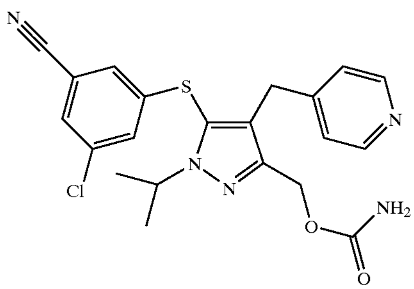 | Carbamic acid [5-(3-chloro-5-cyanophenylthio)-1-isopropyl-4-[(4-pyridyl)methyl]-1H-pyrazol-3-yl]methyl ester |
| 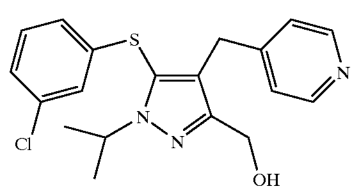 | 5-(3-Chlorophenylthio)-1-isopropyl-4-[(4-pyridyl)methyl]-1H-pyrazole-3-methanol |

The useful activity of the compounds of formula I for the treatment of diseases mediated by the human immunodeficiency virus (HIV) can be demonstrated with the following assay methods.

HIV-1 Reverse Transcriptase Assay: Inhibitor $IC_{50}$ Determination

HIV-1 RT assay was carried out in 96-well Millipore filtermat NOB50 plates using purified recombinant enzyme and a poly(rA)/oligo(dT)$_{16}$ template-primer in a total volume of 50 µL. The assay constituents were 50 mM Tris/HCl, 50 mM NaCl, 1 mM EDTA, 6 mM $MgC_2$, 5 µM dTTP, 0.1 µCi [$^3$H] dTTP, 5 µg/ml poly (rA) pre annealed to 2.5 µg/ml oligo (dT)$_{16}$ and a range of inhibitor concentrations in a final concentration of 10% DMSO. Reactions were initiated by adding 5 nM HIV-1 RT and after incubation at 37° C. for 30 min, they were stopped by the addition of 50 µl ice cold 20% TCA and allowed to precipitate at 4° C. for 30 min. The precipitates were collected by applying vacuum to the plate and sequentially washing with 2×200 µl of 10% TCA and 2×200 µl 70% ethanol. Finally the plates were dried and radioactivity counted in a Wallac Microbeta 1450 after the addition of 15 Vl scintillation fluid per well. $IC_{50's}$ were calculated by plotting % inhibition versus $\log_{10}$ inhibitor concentrations.

Antiviral Assay Method

Anti-HIV antiviral activity was assessed using an adaptation of the method of Pauwels et al. {Pauwels et al., 1988, J Virol Methods 20:309–321}. The method is based on the ability of compounds to protect HIV-infected T lymphoblastoid cells (MT4 cells) from cell-death mediated by the infection. The endpoint of the assay was calculated as the concentration of compound at which the cell viability of the culture was preserved by 50% ('50% inhibitory concentration', $IC_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product.

MT4 cells were prepared to be in logarithmic-phase growth and a total of $2 \times 10^6$ cells infected with the HXB2-strain of HIV at a multiplicity of 0.0001 infectious units of virus per cell in a total volume of between 200–500 microliters. The cells were incubated with virus for one h at 37° C. before removal of virus. The cells are then washed in 0.01 M phosphate buffered saline, pH 7.2 before being resuspensed in culture medium for incubation in culture with serial dilutions of test compound. The culture medium used was RPMI 1640 without phenol red, supplemented with penicillin, streptomycin, L-glutamine and 10% fetal calf serum (GM10).

Test compounds were prepared as 2 mM solutions in dimethyl sulphoxide (DMSO). Four replicate, serial 2-fold dilutions in GM10 were then prepared and 50 microliters amounts placed in 96-well plates over a final nanomolar concentration range of 625–1.22. Fifty microliters GM10 and $3.5 \times 10^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% $CO_2$ in air for 5 d.

A fresh solution of 5 mg/mL MTT was prepared in 0.01 M phosphate buffered saline, pH 7.2 and 20 microliters added to each culture. The cultures were further incubated as before for 2 h. They were then mixed by pipetting up and down and 170 microliters of Triton X-100 in acidified isopropanol (10% v/v Triton X-100 in 1:250 mixture of concentrated HCl in isopropanol). When the formazan deposit was fully solubilized by further mixing, the absorbance (OD) of the cultures was measured at 540 nm and 690 nm wavelength (690 nm readings were used as blanks for artefacts between wells). The percent protection for each treated culture can be calculated from the equation:

$$\% \text{ Protection} = \frac{(\text{OD drug-treated cultures}) - (\text{OD untreated virus control cultures})}{(\text{OD uninfected cultures}) - (\text{OD untreated virus control cultures})} \times 100\%$$

In the assay, compounds of the formula I range in $IC_{50}$ activity from about 0.5 to about 5000 nM, with preferred compounds having a range of about 0.5 to about 750 nM, more preferably about 0.5 to 300 nM, and most preferably about 0.5 to 50 nM.

| Structure | RT $IC_{50}$/nM | HIV $IC_{50}$/nM |
|---|---|---|
| [structure 1] | 62 | 1.3 |
| [structure 2] | 32 | 1 |
| [structure 3] | 714 | 7 |

-continued
| Structure | RT IC$_{50}$/nM | HIV IC$_{50}$/nM |
|---|---|---|
| 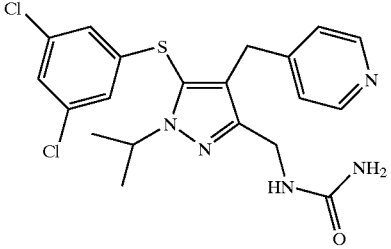 | 44 | 1 |
| 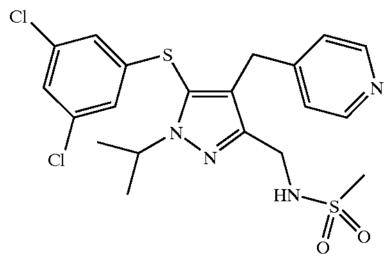 | 7921 | — |
| 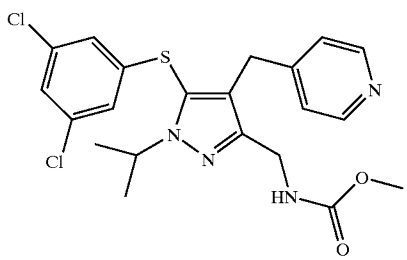 | 525 | — |
| 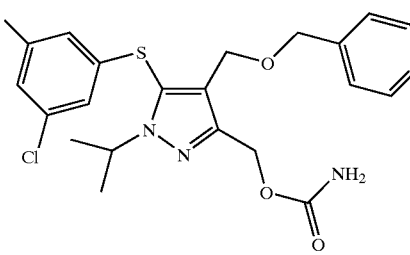 | 99 | 13 |
| 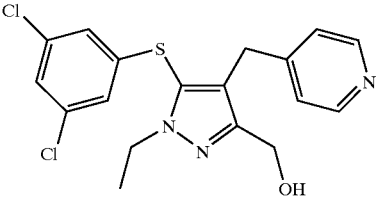 | 183 | 30 |
| 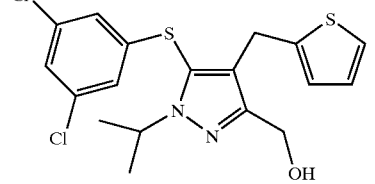 | 434 | 93 |

-continued

| Structure | RT IC$_{50}$/nM | HIV IC$_{50}$/nM |
|---|---|---|
| 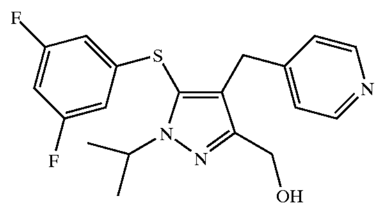 | 206 | 6 |
| 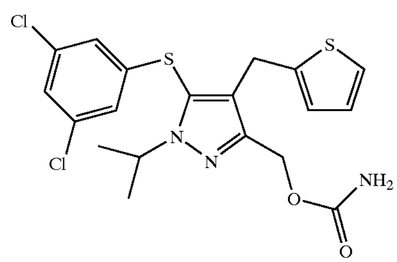 | 211 | 30 |
| 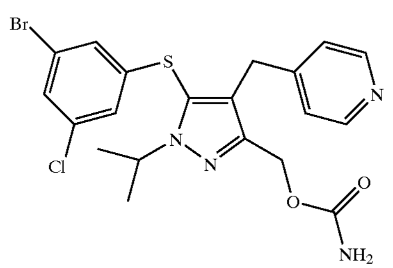 | 31 | 3 |
| 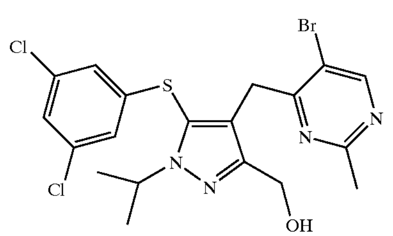 | 518 | — |
| 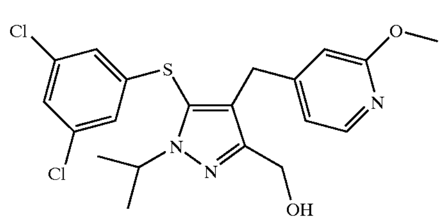 | 51 | 38 |
| 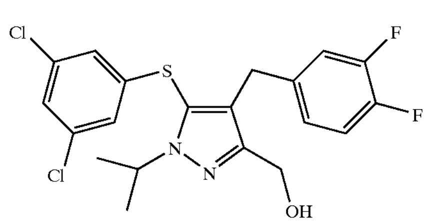 | 123 | — |

| Structure | RT IC$_{50}$/nM | HIV IC$_{50}$/nM |
| --- | --- | --- |
| 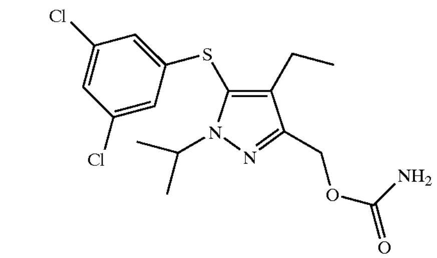 | 61 | — |
| 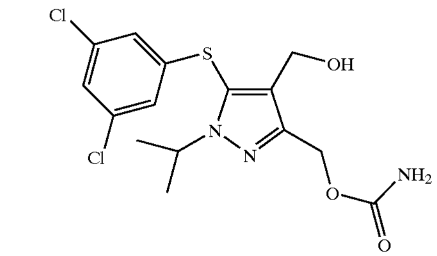 | 6304 | — |
| 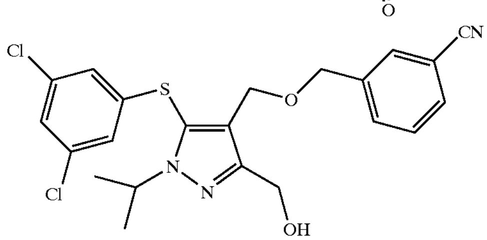 | 250 | — |

The processes for the preparation of compounds of formula I, their ethers and pharmaceutically acceptable salts as well as their compounds, whenever prepared by these processes are also an object of the present invention.

The compounds of the present invention can be prepared in accordance with known methods, e.g. as shown in the following schemes:

Reaction scheme 1

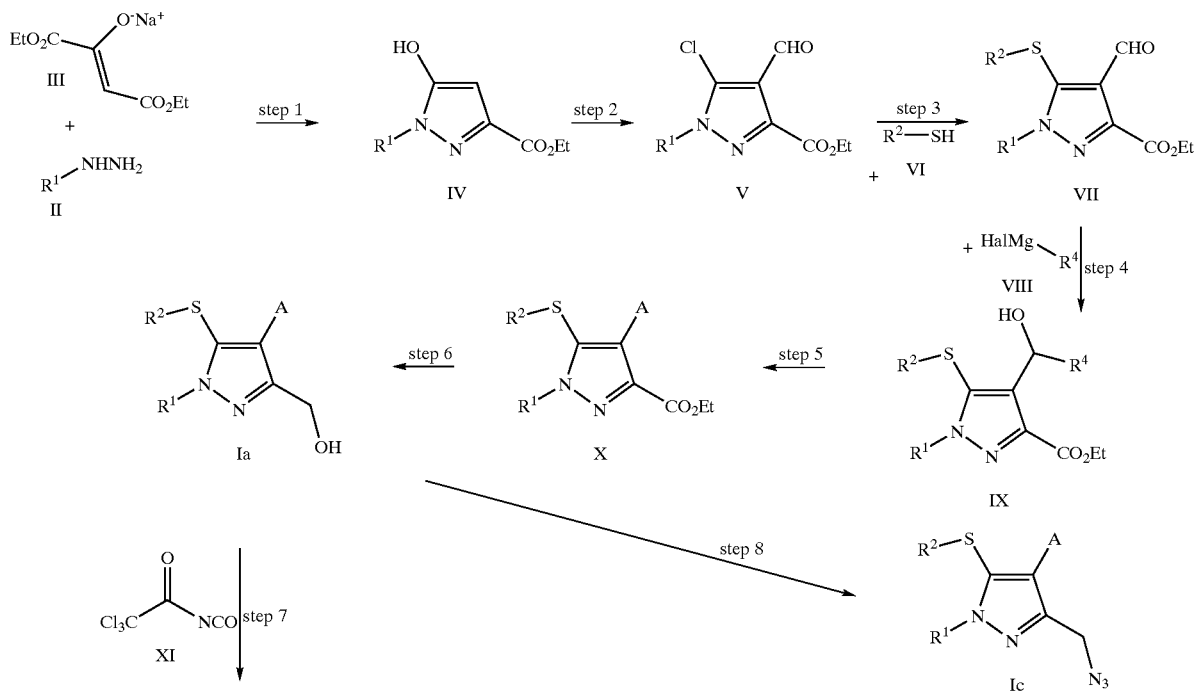

-continued

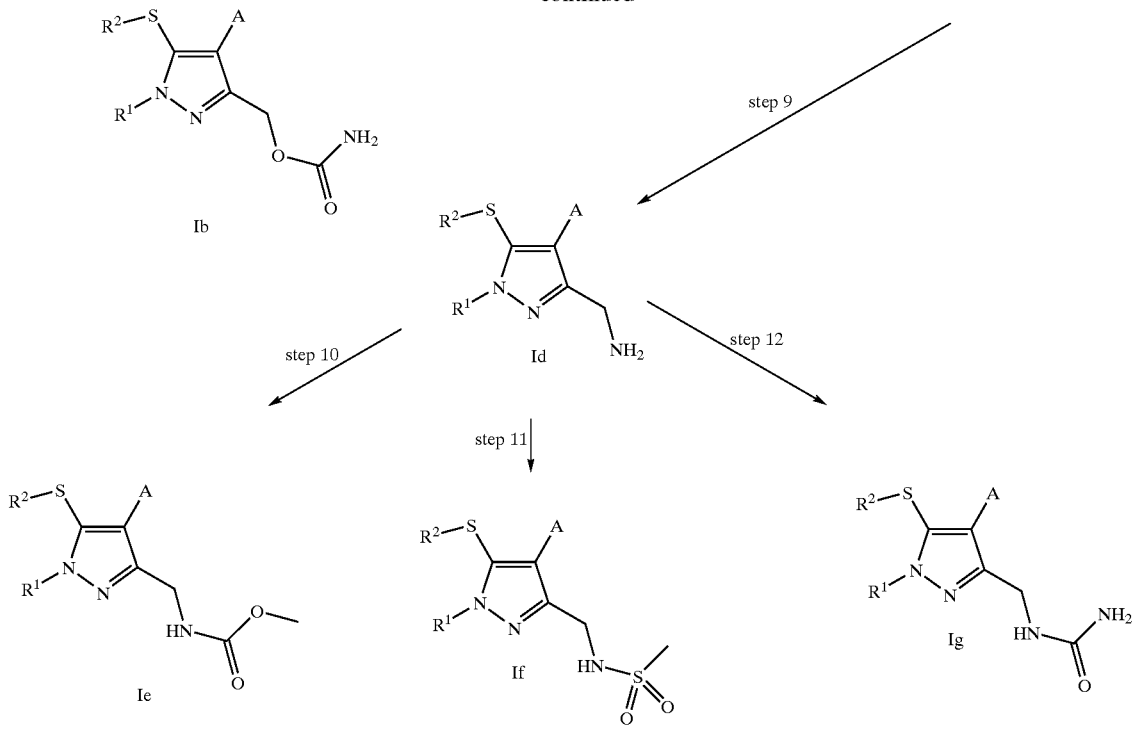

wherein $R^1$ and $R^2$ are as described in formula I, A signifies a group arylmethyl, substituted aryl-methyl, aryl-methoxy-methyl, substituted aryl-methoxy-methyl, heterocyclyl-methyl or substituted heterocyclyl-methyl as described in formula I, $R^4$ is heterocyclyl or substituted heterocyclyl as defined for compounds of formula I and Hal represents chlorine, bromine or iodine.

In reaction scheme 1, step 1 is carried out in that a hydrazine derivative of formula II is reacted with compound of formula III (commercially available from Aldrich or Fluka) to obtain the pyrazole derivative of formula IV. The reaction is conveniently carried out in the presence of a carboxylic acid, for example acetic acid, in an appropriate solvent such as halogenated hydrocarbons (e.g. dichloromethane or trichloromethane) or hydrocarbons (e.g. cyclohexane, methyl cyclohexane, decaline, benzene, toluene, o-xylene, m-xylene or p-xylene), preferably toluene. Further, the reaction is carried out at a reaction temperature from room temperature to boiling temperature of the reaction mixture, preferably at a reaction temperature between about 50° C. and about 150° C.

In step 2 of the reaction scheme, the 5-hydroxy position of pyrazole derivative of formula IV is chlorinated and formylated with a suitable agent. A suitable agent is for example $(COCl)_2$, $SOCl_2$ or $POCl_3$ in combination with N,N-dimethylformamide or N-methylformanilide to obtain the 5-chloro-4-formylpyrazole derivative of formula V. The reaction is conveniently carried out under an inert atmosphere such as nitrogen or argon atmosphere at a reaction temperature from room temperature to boiling temperature of the reaction mixture. Preferably, the reaction is carried out in the presence of $POCl_3$ and N,N-dimethylformamide at a reaction temperature between about 50° C. and about 120° C., more preferred at a reaction temperature between about 90° C. and about 110° C.

In step 3 of the reaction scheme, compound of formula V is reacted with a thiole derivative of formula VI (agents are commercially available or can be synthesized according to methods known from textbooks about organic chemistry e.g. from J. March (1992), "Advanced Organic Chemistry: Reactions, Mechanisms, and Structure", $4^{th}$ ed. John Wiley & Sons), to obtain the pyrazole derivative of formula VII. The reaction is carried out in an appropriate solvent in the presence of a base such as n-BuLi, sodium hydride, trialkylamine (e.g. trimethylamine or triethylamine), potassium carbonate, sodium carbonate, magnesium carbonate, calcium carbonate, preferably potassium carbonate. Further, the reaction is conveniently carried out under an inert atmosphere such as nitrogen or argon atmosphere at a reaction temperature from 0° C. to boiling temperature of the reaction mixture, preferably at a reaction temperature between about 10° C. and about 180° C., more preferred at a reaction temperature from 70° C. to 130° C. of the reaction mixture. Appropriate solvents for the reaction are THF or polar aprotic solvents such as dimethylsulfoxide (DMSO), dimethylacetamide or N,N-dimethylformamide (DMF), preferably DMF.

The thiole derivative of formula VI can as well be derivatised for example in the following way: Commercially available bromo-substituted thiole derivative of formula VI is converted to the corresponding cyano-substituted thiole derivative according to methods known in the art for example textbooks about organic chemistry e.g. from J. March (1992), "Advanced Organic Chemistry: Reactions, Mechanisms, and Structure", $4^{th}$ ed. John Wiley & Sons).

In step 4 of the reaction scheme the pyrazole of formula VII is derivatised with a Grignard reagent $R^4MgHal$ of formula VIII, wherein $R^4$ is heterocyclyl or substituted heterocyclyl as defined for compounds of formula I and Hal represents chlorine, bromine or iodine, preferably chlorine (commercially available or synthesised according to textbooks on organic chemistry e.g. from J. March (1992), "Advanced Organic Chemistry: Reactions, Mechanisms and Structure", $4^{th}$ ed. John Wiley and Sons) to obtain the corresponding substituted hydroxy-methyl-pyrazole derivative of formula IX. The derivatisation reaction is conveniently carried out in an inert solvent for example ethers such as tetrahydrofuran, diethyl ether, dibutyl ether, dioxane, diglyme or a mixture of the mentioned solvents, preferably tetrahydrofuran at a reaction temperature between about −10° C. and about 60° C., preferably at a reaction temperature between about 0° C. and about 40° C., more preferred at room temperature. In general, the derivatisation reaction can also be carried out as described in textbooks about organic chemistry e.g. from J. March (1992), "Advanced Organic Chemistry: Reactions, Mechanisms, and Structure", $4^{th}$ ed. John Wiley & Sons.

In step 5 of the reaction scheme, the substituted hydroxymethyl group of compound of formula IX is reduced to the corresponding methylene group, to obtain the compound of formula X. The reaction is conveniently carried out in the presence of trialkylsilane such as trimethylsilane, triethylsilane or tripropylsilane, preferably triethylsilane, dissolved in mineral acids such as trifluoroacetic acid (TFA) or in Lewis acids such as $SnCl_4$ (described in D. L. Comins et al., Tet. Lett., 1986, 27, 1869). Further, the reaction is carried out at a reaction temperature from 0° C. to 80° C., preferably at a reaction temperature between about 5° C. and about 50° C.

The reduction reaction can also be carried in the presence $P_2I_4$ as described in EP 0627423.

The reduction reaction of the substituted hydroxy methyl group of compound of formula IX can also be carried in the presence of NaI, $(CH_3)_3SiCl$ and HBr or as described in textbooks about organic chemistry e.g. from J. March (1992), "Advanced Organic Chemistry: Reactions, Mechanisms, and Structure", 4th ed. John Wiley & Sons). When the hydroxy group is converted to a leaving group such as a mesylate or sulphonate, preferably a mesylate, the reaction can then be carried out in the presence of Zn and acetic acid (described in J. E. Lynch et al., J. Org. Chem., 1997, 62, 9223–9228).

In step 6 of the reaction scheme, the carboxylic ester group of compound of formula X is reduced to a hydroxy-methyl group, to obtain the corresponding compound of formula Ia. The reaction is carried out in the presence of a reducing agent such as lithium aluminium hydride. Preferably, the reaction is carried out by treating the compound of formula X under nitrogen atmosphere with a reducing agent for example $LiAlH_4$, $LiBH_4$, $BH_3*S(CH_3)_2$, iso-$Bu_2AlH$ or Vitride®, in an inert solvent such as ethers for example anhydrous diethyl ether, THF of dioxane at a reaction temperature from 0° C. to room temperature. More preferred, the reaction is carried out with $LiAlH_4$ and ethers.

In step 7 of the reaction scheme, the hydroxy-methyl function of the pyrazole derivative of formula Ia is derivatised to the primary carbamate of formula Ib, e.g. using trichloroacetyl isocyanate of formula XI. The pyrazole derivative of formula Ia is conveniently dissolved in a suitable organic solvent such as dichloromethane or chloroform and the reagent trichloroacetyl isocyanate of formula XI is added at a reaction temperature from −10° C. to 5° C. The work up involves use of bases such as sodium or potassium carbonate followed by purification using standard procedures. Other methods known in the art can effect this transformation, such as chlorosulfonyl isocyanate or trimethylsilyl isocyanate.

The amino-function of compound of formula Ib can also be mono or dialkylated to obtain the corresponding $C_{1-4}$-alkyl substituted amino function. The reaction is carried out according to methods known from textbooks about organic chemistry e.g. from J. March (1992), "Advanced Organic Chemistry: Reactions, Mechanisms, and Structure", $4^{th}$ ed. John Wiley & Sons).

In step 8 of the reaction scheme, the hydroxy-methyl function of the pyrazole derivative of formula Ia is derivatised to the corresponding azido of formula Ic, e.g. using sodium azide or diphenylphosphoryl azide in standard procedures according to methods known from textbooks on organic chemistry e.g. from J. March (1992), "Advanced Organic Chemistry: Reactions, Mechanisms, and Structure", $4^{th}$ ed. John Wiley & Sons.

In step 9 of the reaction scheme, compound Ic is reduced to a corresponding primary amine of formula Id. The reduction reaction to the primary amine of formula Id is carried out by hydrogenation with standard catalysts such as 10% palladium on carbon in suitable solvents, such as ethyl acetate, methanol or ethanol, or with a trialkyl or aryl phosphine (e.g. trimethylphosphine, triethylphosphine or triphenylphosphine).

In step 10, 11 and 12 of the reaction scheme, the primary amine function of compound of formula Id is acylated, sulfonylated or reacted with isocyanates, to obtain the corresponding compounds of formula Ie, If and Ig according to methods known from textbooks on organic chemistry e.g. from J; March (1992), "Advanced Organic Chemistry: Reactions, Mechanisms, and Structure", $4^{th}$ ed. John Wiley & Sons. These are standard reactions of which there are many combinations of reagents. Acylation (step 10) may be achieved via acid chlorides or other activated carbonyl compounds such as activated carboxylic acids, for example with $C_{1-4}$-alkyl chloroformate (e.g. methyl chloroformate) in the presence of an amine (e.g. trimethylamine or triethylamine, preferably triethylamine) and dichloromethane as solvent at room temperature. The sulfonylation reaction (step 11) is carried out via sulfonyl chlorides (e.g. $C_{1-4}$-alkyl sulfonyl chlorides such as methyl sulfonyl chloride) using a base such as triethylamine, N-methyl morpholine or N-ethyl morpholine, and dichloromethane as solvent at room temperature. The reaction with isocyanates (step 12) is carried out in that compound of formula Id is reacted with trichloroacetyl isocyanate of formula XI as described for step 7, to obtain a compound of formula Ig. The amino-function of compound of formula Ig can also be mono or dialkylated to obtain the corresponding $C_{1-4}$-alkyl substituted amino function. The reaction is carried out according to methods known from textbooks about organic chemistry e.g. from J. March (1992), "Advanced Organic Chemistry: Reactions, Mechanisms, and Structure", $4^{th}$ ed. John Wiley & Sons).

The reactions according to steps 10, 11 and 12 may be conducted in suitable solvents known to those skilled in the art, for example, dichloromethane, chloroform, dioxane, dimethyformamide or tetrahydrofuran.

The NH-function of compounds of formula Ie, If or Ig can be alkylated with $C_{1-4}$-alkyl, preferably methyl or ethyl. The alkylation reaction is carried out according to methods known from textbooks about organic chemistry e.g. from J. March (1992), "Advanced Organic Chemistry: Reactions, Mechanisms, and Structure", $4^{th}$ ed. John Wiley & Sons).

Reaction scheme 2

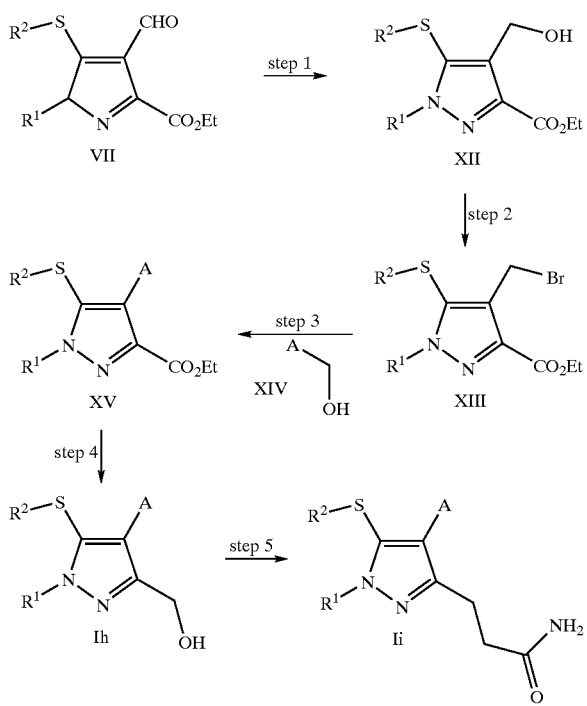

wherein R¹ and R² are as described in formula I and wherein A signifies a group A signifies a group aryl-methyl, substituted aryl-methyl, aryl-methoxy-methyl, substituted aryl-methoxy-methyl, heterocyclyl-methoxy-methyl or substituted heterocyclyl-methoxy-methyl as described in formula I.

In reaction scheme 2, step 1 is carried out in that the aldehyde of formula VII is reduced in the presence of a reducing agent to obtain the corresponding hydroxy-methyl derivative of formula XII. Reducing agents conveniently used for the reaction are preferably sodium borohydride or other reducing agents such as lithium borohydride, sodium triacetoxyborohydride, hydrogen over a catalyst or reducing agents known in the art applied according to known methods described in textbooks on organic chemistry e.g. from J. March (1992), "Advanced Organic Chemistry: Reactions, Mechanisms and Structure", 4$^{th}$ ed. John Wiley and Sons. The reduction reaction is conveniently carried out in an organic solvent for example alcoholic solvents such as methanol, ethanol, propanol, butanol, octanol or cyclohexanol, preferably methanol or ethanol or ethers such as tetrahydrofuran, diethyl ether, dibutyl ether, dioxane or diglyme, preferably tetrahydrofuran or a mixture of the mentioned solvents such as methanol and tetrahydrofuran or ethanol and tetrahydrofuran. The reaction is carried out at a reaction temperature between about −10° C. and about 60° C., preferably at room temperature. The reduction reaction can also be carried out as described in textbooks about organic chemistry e.g. from J. March (1992), "Advanced Organic Chemistry: Reactions, Mechanisms, and Structure", 4$^{th}$ ed. John Wiley & Sons.

In step 2 of the reaction scheme, the hydroxy-methyl function of compound of formula XII is converted to the corresponding bromo-methyl derivative of formula XIII according to standard procedures according to methods known from textbooks on organic chemistry e.g. from J. March (1992), "Advanced Organic Chemistry: Reactions, Mechanisms, and Structure", 4$^{th}$ ed. John Wiley & Sons. A possible method for the preparation of a bromide derivative of formula XIII is by using tetrabromomethane in the presence of triphenylphosphine in dichloromethane, at room temperature.

In step 3 of the reaction scheme, the bromide of formula XIII is reacted with a heterocyclyl-methanol compound of formula XIV to obtain the corresponding pyrazole derivative of formula XV. The reaction is conveniently carried out according to methods known from textbooks on organic chemistry e.g. from J. March (1992), "Advanced Organic Chemistry: Reactions, Mechanisms and Structure", 4$^{th}$ ed. John Wiley and Sons). The reaction is for example carried out in the presence of a base such as sodium hydride, lithium hydride, potassium carbonate or triethylamine in an appropriate organic solvent such as tetrahydrofuran (THF) or polar aprotic solvents like dimethylsulfoxide (DMSO), N,N-dimethylacetamide or N,N-dimethylformamide (DMF), preferably DMF or THF, at a reaction temperature between about −10° C. and about 60° C., preferably at room temperature.

In step 4 of the reaction scheme, the carboxylic ethyl function of compound of formula XV is reduced with an appropriate reducing agent to obtain the corresponding hydroxy-methyl derivative of formula Ih. The reaction is conveniently carried under nitrogen atmosphere with a reducing agent for example LiAlH$_4$, LiBH$_4$, BH$_3$*S(CH$_3$)$_2$, iso-Bu$_2$AlH or Vitride®, in an inert solvent such as ethers for example anhydrous diethyl ether, THF of dioxane at a reaction temperature from 0° C. to room temperature. Preferably, the reaction is carried out with LiAlH$_4$ in an ether such as THF. Subsequently a solution of ammonium chloride is added to yield to a compound of the formula Ih. After the reaction, the product is worked up in a manner known in the art for example extracted with ethyl acetate, dried over anhydrous magnesium sulphate and finally the organic solvent is evaporated.

In step 5 of the reaction scheme, the hydroxy-methyl derivative of formula Ih is derivatised to the primary carbamate of formula Ii. The reaction is carried out with trichloroacetyl isocyanate of formula XI as described for reaction scheme 1 (step 7).

The hydroxy function of compound of formula Ih can also be acylated to obtain the corresponding compound of formula I wherein m=0, X=O and Z=C$_{1-4}$-alkyl. The reaction is carried out according to methods known from textbooks about organic chemistry e.g. from J. March (1992), "Advanced Organic Chemistry: Reactions, Mechanisms, and Structure", 4$^{th}$ ed. John Wiley & Sons).

The hydroxy function of compound of formula Ih can also be transformed to obtain the corresponding compound of formula I wherein m=0, X=O and Z=C$_{1-4}$-alkoxy. The reaction is carried out according to methods known from textbooks about organic chemistry e.g. from J. March (1992), "Advanced Organic Chemistry: Reactions, Mechanisms, and Structure", 4$^{th}$ ed. John Wiley & Sons). The amino-function of compound of formula Ii can also be mono or dialkylated to obtain the corresponding C$_{1-4}$-alkyl substituted amino function. The reaction is carried out according to methods known from textbooks about organic chemistry e.g. from J. March (1992), "Advanced Organic Chemistry: Reactions, Mechanisms, and Structure", 4$^{th}$ ed. John Wiley & Sons).

Compound of formula Ih is reacted according the methods described in reaction scheme 1 (step 8–12) and thereby the corresponding pyrazole derivatives are obtained, wherein A signifies heterocyclyl-methoxy-methyl or substituted heterocyclyl-methoxy-methyl as described in formula I.

Reaction scheme 3

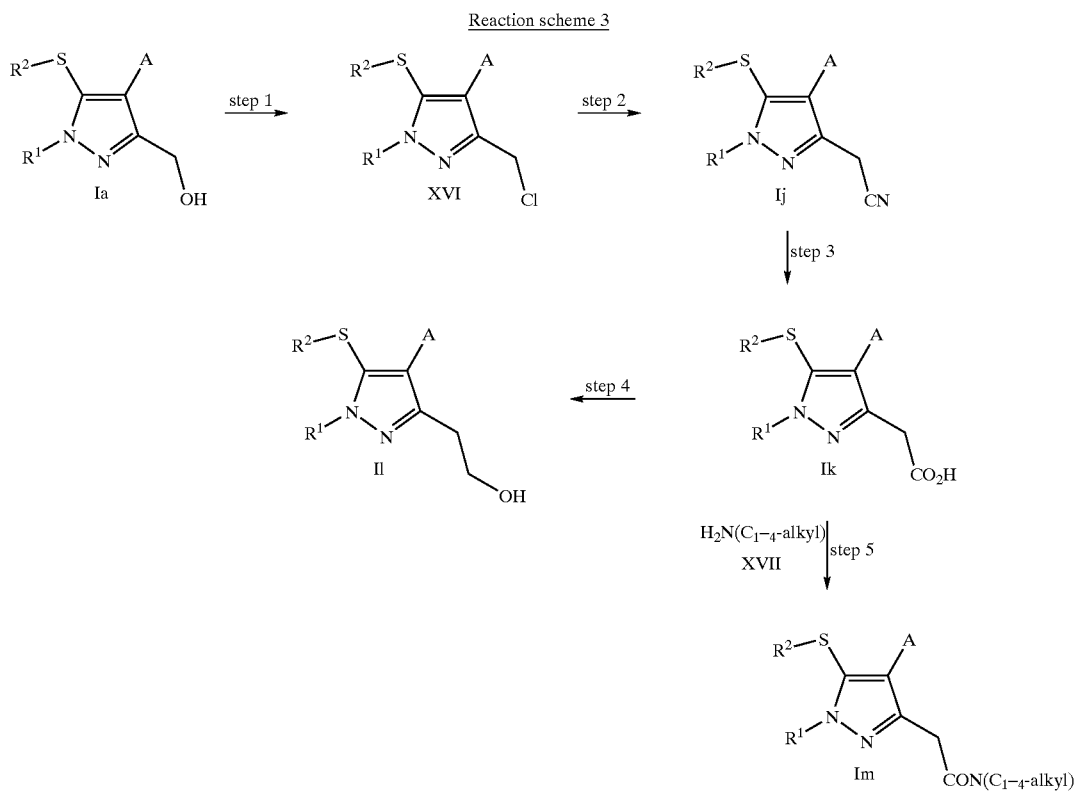

wherein $R^1$, $R^2$ and A are as described in formula I.

In reaction scheme 3, step 1 is carried out in that the hydroxymethyl derivative of formula Ia is chlorinated to give the corresponding chloromethyl derivative of formula XVI according to methods known from textbooks about organic chemistry e.g. from J. March (1992), "Advanced Organic Chemistry: Reactions, Mechanisms, and Structure", $4^{th}$ ed. John Wiley & Sons). The reaction can for example be carried out in the presence of $SOCl_2$ as chlorinating agent. The hydroxymethyl derivative of formula Ia can also be converted to the corresponding iodide, bromide, mesylate or tosylate according to methods known from textbooks about organic chemistry e.g. from J. March (1992), "Advanced Organic Chemistry: Reactions, Mechanisms, and Structure", $4^{th}$ ed. John Wiley & Sons).

In step 2 of the reaction scheme, the chloromethyl derivative of formula XVI is reacted with potassium cyanide in the presence of potassium iodide and DMF, to give the corresponding cyanomethyl derivative of formula Ij, according to methods known from textbooks about organic chemistry e.g. from J. March (1992), "Advanced Organic Chemistry: Reactions, Mechanisms, and Structure", $4^{th}$ ed. John Wiley & Sons). The reaction can as well be carried out with alternative solvents such as DMSO, acetone, acetonitrile, ethanol (and other alcohols)/water mixtures. An optional additive is 18-crown-6.

In step 3 of the reaction scheme, the cyano group of compound of formula Ij is hydrolysed to obtain the corresponding carboxylic acid of formula Ik according to methods known from textbooks about organic chemistry e.g. from J. March (1992), "Advanced Organic Chemistry: Reactions, Mechanisms, and Structure", $4^{th}$ ed. John Wiley & Sons). The reaction is for example carried out in the presence of potassium hydroxide and 1-methoxy-2-hydroxy-ethane. The reaction can as well be carried out in sodium hydroxide or mineral acids, and alternative solvents are methanol, ethanol, water or mixtures thereof.

In step 4 of the reaction scheme, the carboxylic acid group of formula Ik is reduced to obtain the corresponding alcohol of formula II. The reaction is carried out according to methods known from textbooks about organic chemistry e.g. from J. March (1992), "Advanced Organic Chemistry: Reactions, Mechanisms, and Structure", $4^{th}$ ed. John Wiley & Sons), for example in the presence of a reducing agent such as $BH_3$, $BH_3*S(CH_3)_2$ or $LiAlH_4$ (all commercially available) in an inert solvent such as ethers for example anhydrous diethyl ether, THF of dioxane at a reaction temperature from 0° C. to room temperature. More preferred, the reaction is carried out with $BH_3$ in the presence of ethers.

In step 5 of the reaction scheme, the carboxylic acid of formula Ik is derivatised with an amine of formula XVII to obtain the corresponding amide of formula Im according to methods known from textbooks about organic chemistry e.g. from J. March (1992), "Advanced Organic Chemistry: Reactions, Mechanisms, and Structure", $4^{th}$ ed. John Wiley & Sons).

The amino-function of compound of formula Im can also be alkylated to obtain the corresponding $C_{1-4}$-alkyl substituted amino function. The reaction is carried out according to methods known from textbooks about organic chemistry e.g. from J. March (1992), "Advanced Organic Chemistry: Reactions, Mechanisms, and Structure", $4^{th}$ ed. John Wiley & Sons).

Reaction scheme 4

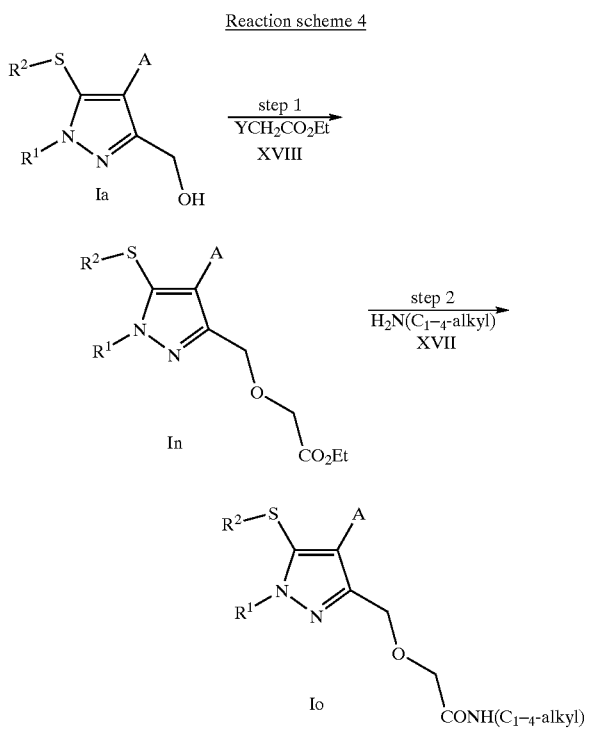

wherein $R^1$, $R^2$ and A are as described in formula I and Y signifies a leaving group.

In reaction scheme 4, step 1 is carried out in that the hydroxymethyl derivative of formula Ia is alkylated with a compound of formula XVIII, wherein Y signifies a leaving group, to obtain the corresponding ether of formula In according to methods known from textbooks about organic chemistry e.g. from J. March (1992), "Advanced Organic Chemistry: Reactions, Mechanisms, and Structure", $4^{th}$ ed. John Wiley & Sons). A leaving group is for example chlorine, bromine, iodine or mesylate (bromine is preferred). The reaction is for example carried out with a compound of formula XVIII in the presence of a base such as sodium hydride or potassium carbonate.

In step 2 of the reaction scheme, the ester of formula In is hydrolysed to obtain the corresponding carboxylic acid and subsequently derivatised, to obtain the corresponding amide of formula Io according to methods known from textbooks about organic chemistry e.g. from J. March (1992), "Advanced Organic Chemistry: Reactions, Mechanisms, and Structure", $4^{th}$ ed. John Wiley & Sons). The derivatisation reaction can be carried out for example with an amine of formula XVII or with ammonia. The amino-function of compound of formula Io can also be alkylated to obtain the corresponding $C_{1-4}$-alkyl substituted amino function. The reaction is carried out according to methods known from textbooks about organic chemistry e.g. from J. March (1992), "Advanced Organic Chemistry: Reactions, Mechanisms, and Structure", $4^{th}$ ed. John Wiley & Sons).

Reaction scheme 5

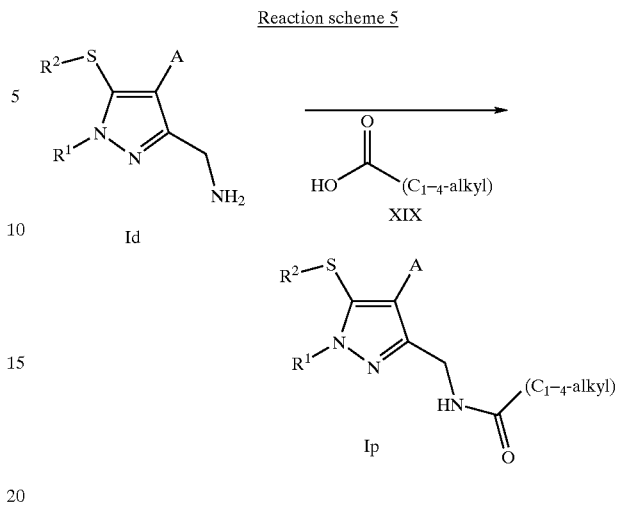

wherein $R^1$, $R^2$ and A are as described in formula I.

In reaction scheme 5, the reaction is carried out in that the primary amine of formula Id is derivatised with caboxylic acid of formula XIX (commercially available or prepared according to methods known in the art), to obtain the corresponding amide of formula Ip. The reaction is carried out according to methods known from textbooks about organic chemistry e.g. from J. March (1992), "Advanced Organic Chemistry: Reactions, Mechanisms, and Structure", $4^{th}$ ed. John Wiley & Sons).

The NH-function of compounds of formula Ip can be alkylated with $C_{1-4}$-alkyl, preferably methyl or ethyl. The alkylation reaction is carried out according to methods known from textbooks about organic chemistry e.g. from J. March (1992), "Advanced Organic Chemistry: Reactions, Mechanisms, and Structure", $4^{th}$ ed. John Wiley & Sons).

Reaction scheme 6

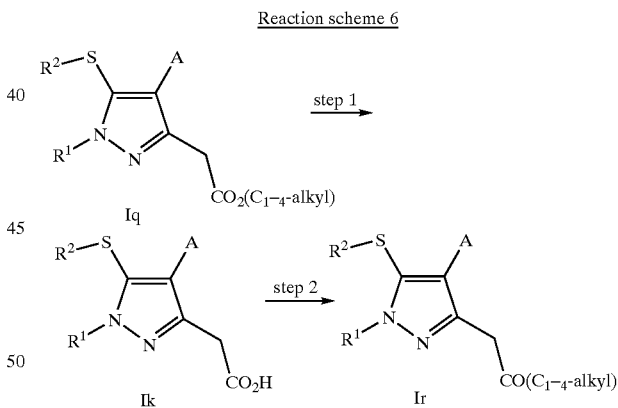

wherein $R^1$, $R^2$ and A are as described in formula I.

In reaction scheme 6, step 1 is carried out in that the carboxylic acid group of compound of formula Ik is alkylated with $C_{1-4}$-alkyl, preferably methyl or ethyl, to obtain compound of formula Iq. The reaction is carried out according to methods known from textbooks about organic chemistry e.g. from J. March (1992), "Advanced Organic Chemistry: Reactions, Mechanisms, and Structure", $4^{th}$ ed. John Wiley & Sons). In a more preferred way, the esterification is carried out via an activated acid derivative (e.g. acid chloride) and an alcohol.

In step 2 of the reaction scheme, the the carboxylic acid group of compound of formula Ik is alkylated with $C_{1-4}$-alkyl, preferably methyl or ethyl, to obtain the corresponding $C_{1-4}$-alkyl-carbonyl-methyl substituted pyrazole compound of formula Ir. The reaction is carried out according to methods known from textbooks about organic chemistry e.g. from J. March (1992), "Advanced Organic Chemistry: Reactions, Mechanisms, and Structure", 4$^{th}$ ed. John Wiley & Sons).

Reaction scheme 7

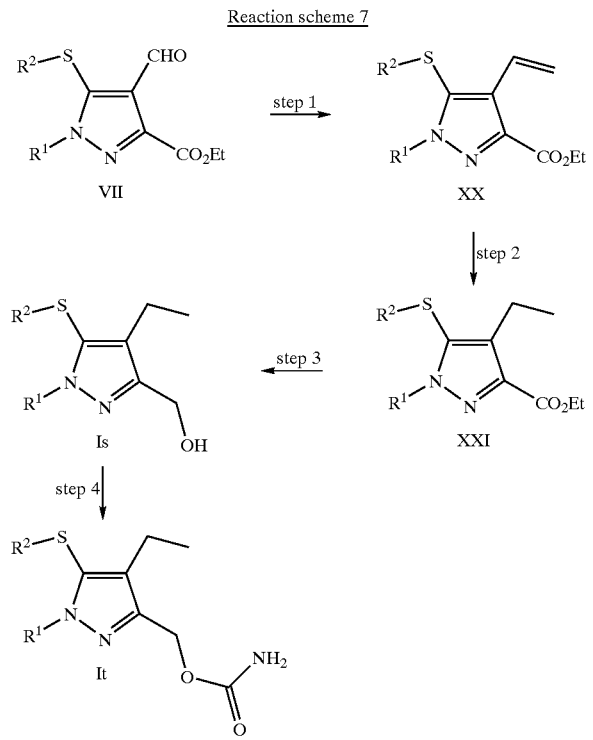

wherein $R^1$ and $R^2$ are as described in formula I.

In reaction scheme 7, step 1 is carried out in that the aldehyde function of compound of formula VII is reacted via a Wittig-Horner reaction with dialkyl phosphonate of formula $(EtO)_2P(=O)(CH_3)$. The reaction is carried out similar the method described in the literature, for example in the presence of a strong base such as n-BuLi or preferably sodium hydride in an organic solvent for example anhydrous ethers such as diethyl ether, dibutyl ether, dioxane, preferably anhydrous tetrahydrofuran under inert atmosphere such as nitrogen or argon atmosphere at a reaction temperature from 0° C. to 80° C., preferably at a reaction temperature between about 5° C. and about 50° C. Optionally, olefinic compound of formula Ic can be obtained through other coupling reactions for example the Wittig reaction.

The Wittig-Horner reaction can also be carried out with dialkyl phosphonates of formula $(EtO)_2P(=O)$—$(C_{1-11}alkyl)$ (commercially available or synthesized according to known methods in the art) to a corresponding olefinic compound of formula XX.

In the second step of the reaction, the olefinic group of compound of formula XX is hydrogenated to the corresponding compound of formula XXI. The reaction is carried out similar to methods described in the literature, for example under hydrogen in the presence of a hydrogenation catalyst in an appropriate solvent at a reaction temperature from 0° C. to 80° C., preferably at a reaction temperature between about 5° C. and about 50° C. The hydrogen pressure can be between about 0 atm and about 100 atm, preferably between about 0 atm and about 50 atm and most preferred between about 0 atm and about 20 atm. The hydrogenation catalyst used for this reaction can be one of the commonly known catalysts such as noble metals (e.g. Pt, Pd or Rh) on supporting materials such as activated carbon or $Al_2O_3$, or generally as described in textbooks about organic chemistry e.g. J. March (1992), "Advanced Organic Chemistry: Reactions, Mechanisms, and Structure", 4$^{th}$ ed. John Wiley & Sons). Preferred hydrogenation catalysts are Pd on activated carbon or Raney-Nickel. Appropriate solvents for the hydrogenation reaction are organic solvent such as alcohols (e.g. methanol, ethanol, propanol, butanol, octanol or cyclohexanol), ethers (e.g. tetrahydrofuran, diethyl ether, dibutyl ether or dioxane), ketones (e.g. acetone, butanone or cyclohexanone), polar aprotic solvents such as dimethylsulfoxide (DMSO) or dimethylacetamide N, esters (e.g. ethyl acetate), halogenated hydrocarbons (e.g. dichloromethane or trichloromethane), hydrocarbons (e.g. cyclohexane, methyl cyclohexane, decaline, benzene, toluene, o-xylene, m-xylene or p-xylene) or a mixtures of the mentioned solvents. Preferred solvents are ester, most preferred solvent is ethyl acetate.

In step 3 of the reaction scheme, the carboxylic ester group of compound of formula XXI is reduced to a hydroxymethyl group, to obtain the corresponding compound of formula Is. The reaction is carried out in the presence of a reducing agent such as lithium aluminium hydride. Preferably, the reaction is carried out by treating the compound of formula XXI under nitrogen atmosphere with a reducing agent for example $LiAlH_4$, $LiBH_4$, $BH_3*S(CH_3)_2$, iso-$Bu_2AlH$ or Vitride®, in an inert solvent such as ethers for example anhydrous diethyl ether, THF of dioxane at a reaction temperature from 0° C. to room temperature. More preferred, the reaction is carried out with $LiAlH_4$ and ethers.

In step 4 of the reaction scheme, the hydroxy-methyl function of the pyrazole derivative of formula Is is derivatised to the primary carbamate of formula It, e.g. using trichloroacetyl isocyanate of formula XI. The pyrazole derivative of formula Ia is conveniently dissolved in a suitable organic solvent such as dichloromethane or chloroform and the reagent trichloroacetyl isocyanate of formula XI is added at a reaction temperature from –10° C. to 5° C. The work up involves use of bases such as sodium or potassium carbonate followed by purification using standard procedures. Other methods known in the art can effect this transformation, such as chlorosulfonyl isocyanate or trimethylsilyl isocyanate.

The compounds of the present invention and pharmaceutical compositions containing the same are useful as chemotherapeutic agents, inhibitors of viral replication and modulators of the immune system, and can be used for the treatment of diseases mediated by the human immunodeficiency virus (HIV) other viral diseases such as retroviral infections (either alone or in combination with other antiviral agents such as interferon or derivatives thereof, such as conjugates with polyethylene glycol).

They can be used alone, or in combination with other therapeutically active agents, for example, an immunosuppressant, a chemotherapeutic agent, an anti-viral agent, an antibiotic, an anti-parasitic agent, an anti-inflammatory agent, an anti-fungal agent and/or an anti-vascular hyperproliferation agent.

It will be understood that references herein to treatment extend to prophylaxis as well as to treatment of existing conditions. Treatment of a disease or condition, as used herein, also includes preventing, inhibiting, regressing, reversing, alleviating or relieving the disease or condition, or the clinical symptoms thereof. The term "subject" as used herein refers to animals, including humans and other mammals.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The pyrazole derivatives provided by the present invention can be used together with a therapeutically inert carrier as medicaments in the form of pharmaceutical preparations. The pharmaceutical preparations can be administered enterally, such as orally, in the form of tablets, coated tablets, dragees, hard and soft gelatine capsules, solutions, emulsions or suspensions, or nasally, e.g. in the form of nasal sprays. They can also be administered rectally, e.g. in the form of suppositories, or parenterally, (e.g. intramuscularly, intravenously, or subcutaneously), for example, in the form of injection solutions.

For the manufacture of pharmaceutical preparations the pyrazole derivatives can be formulated with therapeutically inert, inorganic or organic carriers.

Lactose, corn starch or derivatives thereof, talc, stearic acid or its salts can be used, for example, as such carriers for tablets, coated tablets, dragees and hard gelatine capsules.

Suitable carriers for soft gelatine capsules are, for example, vegetable oils, waxes, fats, semi-solid and liquid polyols and the like.

Suitable carriers for the manufacture of injection solutions are, for example, water, saline, alcohols, polyols, glycerine, vegetable oils and the like. Natural or hardened oils, waxes, fats, semi-liquid or liquid polyols and the like are suitable carriers for the manufacture of suppositories. The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents such as those mentioned above.

The pyrazole derivatives provided by the invention in the treatment of an immune mediated condition or disease, a viral disease, a bacterial disease, a parasitic disease, an inflammatory disease, a hyperproliferative vascular disease, a tumor, or cancer.

The dosage can vary within wide limits and will, of course, be adjusted to the individual requirements in each particular case.

Dosage levels of between about 0.01 and about 100 mg/kg body weight per day in monotherapy and/or in combination therapy are commonly administered from about 1 to 5 times per day. A typical preparation will contain from about 5% to 95% active compound (w/w). The daily dosage can be administered as a single dosage or in divided dosages.

The pyrazole derivatives provided by the present invention or the medicaments thereof may be for use in monotherapy and/or combination therapy, i.e. the treatment may be in conjunction with the administration of one or more additional therapeutically active substance(s). When the treatment is combination therapy, such administration may be concurrent or sequential with respect to that of the pyrazole derivatives of the present invention. Thus, concurrent administration, as used herein, includes administration of the agents in conjunction or combination, together, or before or after each other.

With regard to the starting materials that are known compounds some of these may be purchased from commercial suppliers. Other starting materials that are known and their analogues can be prepared by methods well known in the art. Examples of compounds available from commercial suppliers, and citations to the synthesis of other compounds and their analogues are provided in the following:

The described NMR spectra were recorded on a Bruker DRX 400 MHz spectrometer with the probe temperature set at 300 K.

The mass spectra indicated by "(M+; EI)", were recorded under electron impact conditions (EI), on a THERMO-QUEST MAT95 S with a source temperature of 200° C. Other mass spectra were recorded under electrospray ionization spectra (ESI) conditions, on one of the following machines:

THERMOQUEST SSQ 7000 [Solvent 0.085% TFA in 90% Acetonitrile/water; flow rate 100 microliters/minute; capillary 250° C.; spray voltage 5 KV; sheath gas 80 psi], or LC-MS system (liquid chromatograph coupled to mass spectrum) THERMOQUEST TSQ 7000 ELECTROSPRAY or MICROMASS PLATFORM ELECTROSPRAY [Solvent 0.1% TFA in water or 0.085% TFA in 90% acetonitrile/water or 0.085% TFA in acetonitrile].

In the following examples the abbreviations used have the following significations:

min minute(s)

h hour(s)

d day(s)

Vitride® sodium bis(2-methoxyethoxy)aluminum hydride (Fluka)

The following examples illustrate the present invention:

EXAMPLE 1

5-(3,5-Dichlorophenylthio)-1-isopropyl-4-[(4-pyridyl)methyl]-1H-pyrazole-3-methanol A solution containing 0.4 ml of lithium aluminium hydride (1M solution in THF) in 2 ml of anhydrous tetrahydrofuran at 0° C. under nitrogen was treated dropwise with a solution of 154 mg of 5-(3,5-Dichloro-phenylsulfanyl)-1-isopropyl-4-pyridin-4-ylmethyl-1H-pyrazole-3-carboxylic acid ethyl ester in 2 ml of anhydrous tetrahydrofuran. The mixture was stirred at 0° C. for 0.5 h then treated with 0.012 ml of water, 0.012 ml of 2N sodium hydroxide solution and then 0.018 ml of water. The mixture was stirred for 0.5 h at 0° C.; the mixture was filtered and then the solvent removed. The residue was purified by flash chromatography on silica gel using dichloromethane/methanol (1:19) for the elution to give 90 mg of 5-(3,5dichlorophenylthio)-1-isopropyl-4-[(4-pyridyl)methyl]-1H -pyrazole-3-methanol as a white gum. Mass spectrum (ESI) m/z 408 [M+H]$^+$. $^1$H NMR (DMSO) 1.30 (d, 6H), 3.90 (s, 2H), 4.55 (d, 2H), 4.72 (m, 1H), 5.30 (t, 1H), 6.85 (s, 2H), 7.15 (d, 2H), 7.35 (s, 1H), 8.30 (d, 2H).

The starting material 5-(3,5-dichlorophenylthio)-1-isopropyl-4-[(4-pyridyl)methyl]-1H-pyrazole-3-carboxylic acid ethyl ester was prepared as follows:

(A) A solution containing 15.01 g of tert-butyl carbazate in 80 ml of acetone was stirred at 60° C. for 2 h. The mixture was evaporated under reduced pressure to give 19.25 g of N'-isopropylidene-hydrazinecarboxcylic acid tert-butyl ester as a white solid which was used without further purification.

(B) A solution containing 19.25 g of N'-isopropylidene-hydrazinecarboxylic acid tert-butyl ester in 100 ml of methanol was treated with 12 g of 5% Pt/C catalyst. The mixture was then hydrogenated at atmospheric pressure for 15 h. The mixture was then filtered through hyflo and solvent removed to give 16.77 g of N'-isopropyl-hydrazinecarboxcylic acid tert-butyl ester as a colourless oil which was used without further purification.

(C) A solution containing 15.6 g of N'-isopropyl-hydrazinecarboxylic acid tert-butyl ester in 100 ml of 4N HCl in ethyl acetate was stirred at room temperature for 15 h. The mixture was then evaporated to give 13 g of isopropylhydrazine dihydrochloride which was used without further purification.

(D) A solution containing 29 g of isopropylhydrazine dihydrochloride in 150 ml of water was added dropwise to a stirred solution of 41.7 g of diethyl oxalacetate, sodium salt in 300 ml of acetic acid and 150 ml of toluene. The mixture was heated at 140° C. for 5 h. The mixture was left to cool to room temperature and then the solvent was evaporated under reduced pressure and the residue azeotroped with toluene. The residue was partitioned between dichloromethane and water. The dichloromethane extract was washed with brine, dried over anhydrous magnesium sulphate, filtered and evaporated under reduced pressure. The residue was triturated with diethyl ether to give a white solid which was filtered then washed three times with cold diethyl ether and dried to give 11.1 g of 5-hydroxy-1-isopropyl-1H-pyrazole-3-carboxylic acid ethyl ester as a white solid which was used without further purification.

(E) 8 g of 5-hydroxy-1-isopropyl-1H-pyrazole-3-carboxylic acid ethyl ester was added portionwise to a preformed mixture of 3.44 ml of dimethylformamide and 94 ml of phosphorus oxychloride at 0° C. under nitrogen. The mixture was then heated at 100° C. for 20 h. The mixture was evaporated under reduced pressure, the residue poured into ice-cold saturated sodium hydrogen carbonate and then extracted three times with dichloromethane. The combined extracts were washed with brine then dried over anhydrous magnesium sulphate, filtered and evaporated to give 9.1 g of 5-chloro-4-formyl-1-isopropyl-1H-pyrazole-3-carboxylic acid ethyl ester as a light brown solid which was used without further purification. Mass spectrum (ESI) m/z 245 [M+H]$^+$.

(F) A solution containing 6 g of 5-chloro-4-formyl-1-isopropyl-1H-pyrazole-3-carboxylic acid ethyl ester in 10 ml of anhydrous dimethyl formamide was treated at room temperature with 5.28 g of 3,5-dichlorothiophenol and 4.07 g of potassium carbonate. The mixture was then heated at 60° C. for 1 h before being left to cool to room temperature. The solvent removed under reduced pressure and the residue partitioned between dichloromethane and water. The organic extract was washed with brine then dried over anhydrous magnesium sulphate, filtered and evaporated. The residue was purified by flash chromatography on silica gel using diethyl ether/petoleum ether (1:4 to 1:3) for the elution to give 8.53 g of 5-(3,5-dichlorophenylthio)-4-formyl-1-isopropyl-1H-pyrazole-3-carboxylic acid ethyl ester as a yellow oil. Mass spectrum (ESI) m/z [M+H]$^+$.

(G) 582 mg of 4-Bromopyridine hydrochloride was treated with a 5% sodium carbonate solution then extracted three times with anhydrous diethyl ether. The combined extracts were then dried over anhydrous magnesium sulphate, filtered and evaporated to give a colourless oil. The colourless oil was dissolved in 3 ml of anhydrous terahydrofuran under nitrogen at room temperature and then treated with 1.5 ml of isopropylmagnesium chloride (2M solution in tetrahydrofuran). The mixture was stirred at room temperature for 1.5 h and then treated with a solution of 5-(3,5-dichlorophenylsulfanyl)-4-formyl-1-isopropyl-1H-pyrazole-3-carboxylic acid ethyl ester in 3 ml of anhydrous tetrahydrofuran. The mixture was then stirred for 1 h. The mixture was then treated with water and extracted with dichloromethane three times. The combined extracts were washed with brine then dried over anhydrous magnesium sulphate, filtered and evaporated. The residue was purified by flash chromatography on silica gel using ethyl acetate/petroleum ether (1:1 to 2:1) for the elution to give 690 mg of 5-(3,5-dichlorophenylsulfanyl)-4-[(4-pyridyl)hydroxymethyl]-1-isopropyl-1H-pyrazole-3-carboxylic acid ethyl ester as a pale yellow oil. Mass spectrum (EST) m/z 466 [M+H]$^+$.

(H) A solution containing 660 mg of diphosphorus tetraiodide in 5 ml of anhydrous toluene was heated at 80° C. for 20 min under nitrogen in the dark. The mixture was then treated dropwise with a solution of 674 mg of 5-(3,5-dichlorophenylthio)-4-[(4-pyridyl)hydroxymethyl]-1-isopropyl-1H-pyrazole-3-carboxylic acid ethyl ester in 5 ml of anhydrous toluene. The mixture was stirred at 80° C. for 1 h and then left to cool to room temperature. The mixture was treated with 10 ml of a 10% solution of sodium bisulphite and then stirred at room temperature for 1 h. The mixture was partitioned between ethyl acetate and water then extracted three times. The combined extracts were washed with brine then dried over anhydrous magnesium sulphate, filtered and evaporated. The residue was purified by flash chromatography on silica gel using ethyl acetate/petroleum ether (1:1 to 2:1) for the elution to give 483 mg of 5-(3,5-dichlorophenylthio)-1-isopropyl-4-[(4-pyridyl)methyl]-1H-pyrazole-3-carboxylic acid ethyl ester as a pale yellow gum. Mass spectrum (ESI) m/z 450 [M+H]$^+$.

Examples 1a–1e

The compounds shown in table 2 were prepared in a manner analogous to that described in example 1

TABLE 2

| Example | Structure | MS (ES) (M + H)$^+$ |
|---|---|---|
| 1a | 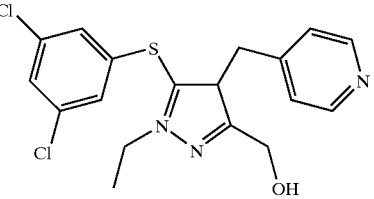 | 394.35 |

TABLE 2-continued

| Example | Structure | MS (ES) (M + H)+ |
|---|---|---|
| 1b | 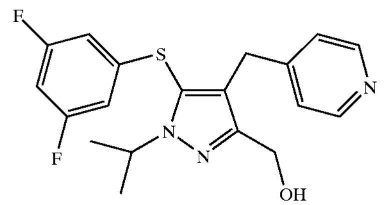 | 376.36 |
| 1c | 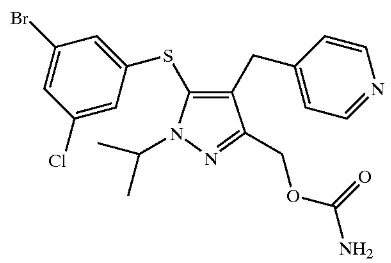 | 454.27 |
| 1d | 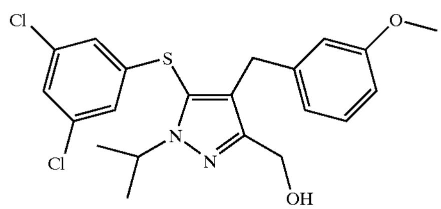 | 437.22 |
| 1e | 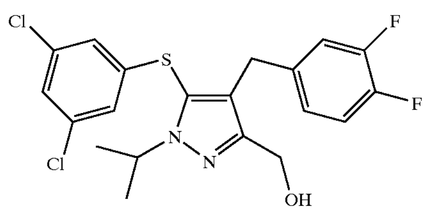 | 443 (M+) |
| 1f | 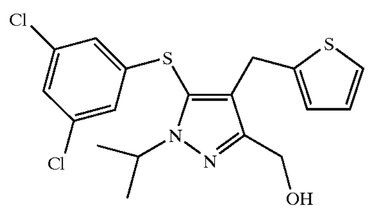 | 413.27 |
| 1g | 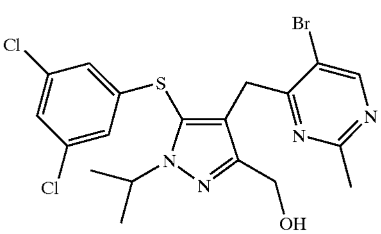 | 501.16 |

EXAMPLE 2

Carbamic acid [5-(3,5-dichlorophenylthio)-1-isopropyl-4-[(4-pyridyl)methyl]-1H-pyrazol-3-yl] methyl ester A solution containing 100 mg of 5-(3,5-dichlorophenylthio)-1-isopropyl-4-[(4-pyridyl)methyl]-1H-pyrazole-3-methanol in 3 ml of anhydrous dichloromethane was stirred under nitrogen at 0° C. while 35 μl of trichloroacetyl isocyanate was added dropwise. The mixture was stirred at 0° C. for 2 h. The mixture was evaporated under reduced pressure and then the residue was treated with 2 ml of methanol, 1 ml water and 100 mg of potassium carbonate under nitrogen at 0° C. The mixture was then stirred at room temperature for 1 h. The mixture was partitioned between ethyl acetate and water then extracted with ethyl acetate three times. The combined extracts were washed with brine then dried over anhydrous magnesium sulphate, filtered and evaporated. The residue was purified by flash chromatography on silica gel using methanol/dichloromethane (1:49) for the elution to give 67 mg of carbamic acid [5-(3,5-dichlorophenylthio)-1-isopropyl-4-[(4-pyridyl)methyl]-1H-pyrazol-3-yl]methyl ester as a white solid. Mass spectrum (ESI) m/z 451 [M+H]$^+$. $^1$H NMR (DMSO) 1.30 (d, 6H), 3.91 (s, 2H), 4.77 (m, 1H), 5.05 (s, 2H), 6.55 (br s, 1H), 6.78 (br s, 1H), 6.79 (s, 2H), 7.08 (d, 2H), 7.39 (s, 1H), 8.30 (d, 2H).

Examples 2a–2e

The compounds shown in table 3 were prepared in a manner analogous to that described in example 2

TABLE 3

| Example | Structure | MS (ES) (M + H)$^+$ |
|---|---|---|
| 2a | 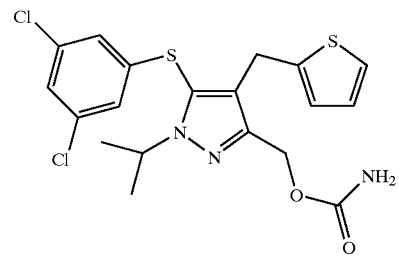 | 456.27 |
| 2b | 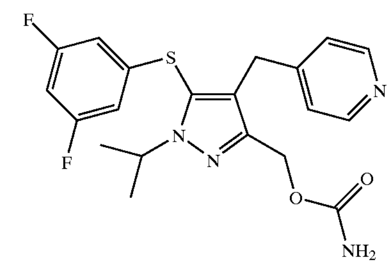 | 419 |
| 2c | 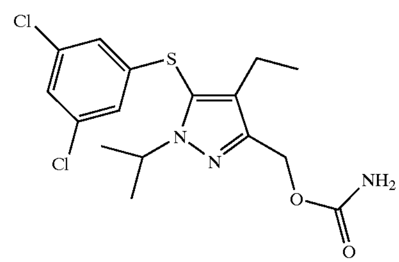 | 333 (M$^+$) |
| 2d | 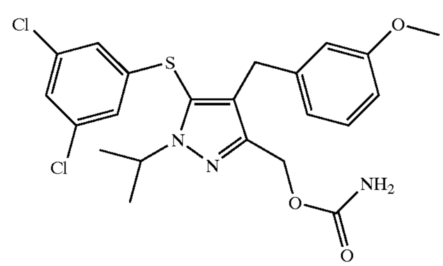 | 480.40 |
| 2e | 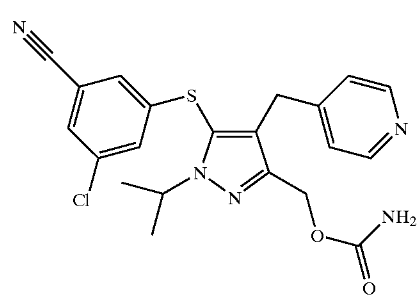 | 442.31 |

EXAMPLE 3

Methylcarbamic acid [5-(3,5-dichlorophenylthio)-1-isopropyl-4-[(4-pyridyl)methyl]-1-1H-pyrazol-3-yl] methyl ester

A solution containing 45 mg of 5-(3,5-dichlorophenylthio)-1-isopropyl-4-[(4-pyridyl)methyl]-1H-pyrazole-3-methanol in 4 ml of anhydrous dichloromethane under nitrogen at room temperature was treated with 0.017 ml of triethylamine and 0,007 ml of methyl isocyanate. The mixture was stirred at room temperature for 1 h. The mixture was partitioned between ethyl acetate and water then extracted with dichloromethane three times. The combined extracts were washed with brine then dried over anhydrous magnesium sulphate, filtered and evaporated. The residue was purified by flash chromatography on silica gel using methanol/dichloromethane (0:1 to 1:49) for the elution to give 36 mg of methylcarbamic acid [5-(3,5-dichlorophenylthio)-1-isopropyl-4-[(4-pyridyl)methyl]-1H-pyrazol-3-yl]methyl ester as a yellow gum. Mass spectrum (ESI) m/z 465 [M+H]$^+$. $^1$H NMR (DMSO) 1.30 (d, 6H), 2.55 (d, 3H), 3.90 (s, 2H), 5.05 (s, 2H), 6.77 (s, 2H), 7.05 (d, 2H), 7.12 (m, 1H), 7.37 (s, 1H), 8.30 (d, 2H).

EXAMPLE 4

5-(3,5-Dichlorophenylthio)-1-isopropyl-4-[(4-pyridyl)methyl]-1H-pyrazole-3-methylamine

A solution containing 120 mg of 4-[3-Azidomethyl-5-(3,5-dichloro-phenylsulfanyl)-1-isopropyl-1H-pyrazol-4-ylmethyl]-pyridine in 5 ml of ethyl acetate was treated with 20 mg of 10% palladium on charcoal and then hydrogenated at atmospheric pressure for 2.0 h. The mixture was filtered and then the solvent was removed under reduced pressure. The residue was purified by flash chromatography on silica gel using methanol/dichloromethane (1:9) for the elution to give 61 mg of 5-(3,5-dichlorophenylthio)-1-isopropyl-4-[(4-pyridyl)methyl]-1H-pyrazole-3-methylamine as a pale yellow oil. Mass spectrum (ESI) m/z 407 [M+H]$^+$. $^1$H NMR (DMSO) 1.30 (d, 6H), 3.72 (s, 2H), 3.90 (s, 2H), 4.70 (m, 1H), 6.78 (s, 2H), 7.10 (d, 2H), 7.37 (s, 1H), 8.30 (d, 2H).

The starting material 4-[3-azidomethyl-5-(3,5-dichlorophenylthio)-1-isopropyl-1H-pyrazol-4-ylmethyl]pyridine was prepared as follows:

(A) A solution containing 108 mg of 5-(3,5-dichlorophenylthio)-1-isopropyl-4-[(4-pyridyl)methyl]-1H-pyrazole-3-methanol in 5 ml of anhydrous dichloromethane at −78° C. under nitrogen was treated with 45 μl of thionyl chloride. The mixture was stirred for 1 h and left to warm to room temperature. The solvent was removed under reduced pressure and the residue was azeotroped with toluene to give 120 mg of 4-[3-chloromethyl-5-(3,5-dichloro-phenylthio)-1-isopropyl-1H-pyrazol-4-ylmethyl]pyridine hydrochloride as a white solid which was used without further purification. Mass spectrum (ESI) 426 [M+H]$^+$.

(B) To a solution of 120 mg of 4-[3-chloromethyl-5-(3,5-dichlorophenylthio)-1-isopropyl-1H-pyrazol-4-ylmethyl] pyridine hydrochloride in 1 ml of anhydrous dimethylformamide stirred at room temperature was added 85 mg of sodium azide. The mixture was stirred for 1 h. The mixture was partitioned between diethyl ether and water then extracted three times. The combined extracts were reduced under reduced pressure to give 120 mg of 4-[3-azidomethyl-5-(3,5-dichlorophenylthio)-1-isopropyl-1H-pyrazol-4-ylmethyl]pyridine as a yellow oil which was used without any further purification. Mass spectrum (ESI) 433 [M+H]$^+$.

EXAMPLE 5

1-[[5-(3,5-Dichlorophenylthio)-1-isopropyl-4-[(4-pyridyl)methyl]-1H-pyrazol-3-yl]methyl]urea

A solution containing 41 mg of 5-(3,5-dichlorophenylthio)-i-isopropyl-4-[(4-pyridyl)methyl]-1H-pyrazole-3-methylamine in 2 ml of anhydrous dichloromethane at 0° C. under nitrogen was treated with 0.014 ml of trichloroacetyl isocyanate. The mixture was stirred for 1.5 h. The solvent was removed under reduced pressure and then the residue treated with 2 ml of methanol, 1 ml of water and 100 mg of potassium carbonate at 0° C. The mixture was stirred for 0.33 h and then a further 100 mg of potassium carbonate was added. The mixture was stirred for 1.5 h. The mixture was partitioned between ethyl acetate and water then extracted with ethyl acetate three times. The combined extracts were washed with brine then dried over anhydrous magnesium sulphate, filtered and evaporated. The residue was purified by flash chromatography on silica gel using methanol/dichloromethane (1:9) for the elution to give 20 mg of 1-[[5-(3,5-dichlorophenylthio)-1-isopropyl-4-[(4-pyridyl)methyl]-1H-pyrazol-3-yl]methyl]urea as a white solid. Mass spectrum (ESI) m/z 465 [M+H]$^+$. $^1$H NMR (DMSO) 1.30 (d, 6H), 3.90 (s, 2H), 4.25 (d, 2H), 4.70 (m, 1H), 4.50 (br s, 1H), 6.40 (t, 1H), 6.75 (s, 2H), 7.07 (d, 2H), 7.36 (s, 1H), 8.30 (d, 2H).

EXAMPLE 6

N-[[5-(3,5-Dichlorophenylthio)-1-isopropyl-4-[(4-pyridyl)methyl]-1H-pyrazol-3-yl]methyl] methanesulfonamide

A solution containing 35 mg of 5-(3,5-dichlorophenylthio)-1-isopropyl-4-[(4-pyridyl)methyl]-1H-pyrazole-3-methylamine in 3 ml of anhydrous dichloromethane at room temperature under nitrogen was treated with 0.024 ml of triethylamine and 0.007 ml of methane sulphonyl chloride. The mixture was stirred at room temperature for 0.5 h. The mixture was partitioned between dichloromethane and saturated sodium hydrogen carbonate then extracted three times. Combined extracts were washed with brine then dried over anhydrous magnesium sulphate, filtered and evaporated. The residue was purified by flash chromatography on silica gel using methanol/dichloromethane (1:19) for the elution to give 21 mg of N-[[5-(3,5-dichlorophenylthio)-1-isopropyl-4-[(4-pyridyl)methyl]-1H-pyrazol-3-yl]methyl]methanesulfonamide as a brown solid. Mass spectrum (ESI) m/z 465 [M+H]$^+$. $^1$H NMR (DMSO) 1.30 (d, 6H), 2.90 (s, 3H), 3.92 (s, 2H), 4.20 (d, 2H), 4.73 (m, 1H), 6.89 (s, 2H), 7.11 (d, 2H), 7.38 (s, 1H), 7.56 (t, 1H), 8.30 (d, 2H).

EXAMPLE 7

Methyl [[5-(3,5-dichlorophenylthio)-1-isopropyl-4-[(4-pyridyl)methyl]-1H-pyrazol-3-yl]methyl] carbamate

A solution containing 21 mg of 5-(3,5-dichlorophenylthio)-1-isopropyl-4-[(4-pyridyl)methyl]-1H-pyrazole-3-methylamine in 2 ml of dichloromethane at room temperature under nitrogen was treated with 0.014 ml of triethylamine and 0.004 ml of methyl chloroformate. The mixture was stirred for 1 h. The mixture was partitioned between dichloromethane and sodium hydrogen carbonate then extracted three times. Combined extracts were washed with brine then dried over anhydrous magnesium sulphate, filtered and evaporated. The residue was purified by flash chromatography on silica gel using methanol/dichloromethane (1:19) for the elution to give 15 mg of methyl [[5-(3,5-dichlorophenylthio)-1-isopropyl-4-[(4-pyridyl)methyl]-1H-pyrazol-3-yl]methyl]carbomate as a yellow solid. Mass spectrum (ESI) m/z 485 [M+H]$^+$. $^1$H NMR (DMSO) 1.30 (d, 6H), 3.45 (s, 3H), 3.90 (s, 2H), 4.28 (d, 2H), 4.75 (m, 1H), 6.80 (s, 2H), 7.13 (d, 2H), 7.36 (s, 1H), 7.65 (br t, 1H), 8.30 (d, 2H).

EXAMPLE 8

5-(3,5-Dichlorophenylthio)-1-isopropyl-4-[(4-pyridyl)methoxymethyl]-1H-pyrazole-3-methanol To a solution of lithium aluminium hydride (0.2 ml of 1M solution in tetrahydrofuran) in tetrahydrofuran at 0° C. was added a solution of 80 mg of 5-(3,5-dichlorophenylthio)-1-isopropyl-4-[4-(pyridyl)methoxymethyl]-1H-pyrazole-3-carboxylic acid ethyl ester dropwise. The mixture was stirred at 0° C. for 0.5 h before water (0.007 ml), 2M sodium hydroxide solution (0.007 ml) then further water (0.011 ml) were added. The mixture was filtered and the solvent was removed. The residue was purified by flash chromatography on silica gel using methanol/dichloromethane for the elution to give 33 mg of 5-(3,5-dichlorophenylthio)-1-isopropyl-4-[(4-pyridyl)methoxymethyl]-1H-pyrazole-3-methanol as a colourless gum. Mass spectrum (ESI) m/z 438 [M]$^+$. $^1$H NMR (DMSO-d6) 1.30 (d, 6H), 4.50 (s, 2H), 4.55 (s, 2H), 4.58 (br s, 2H), 4.80 (m, 1H), 5.18 (br s, 1H), 7.08 (m, 2H), 7.18 (d, 2H), 7.45 (m, 1H), 8.45 (d, 2H).

The starting material 5-(3,5-dichlorophenylthio)-1-isopropyl-4-[4-(pyridyl)methoxymethyl]-1H-pyrazole-3-carboxylic acid ethyl ester was prepared as follows:

(A) To a solution of 530 mg of 5-(3,5-dichlorophenylthio)-4-formyl-1-isopropyl-1H-pyrazole-3-carboxylic acid ethyl ester in methanol (5 ml) at 0° C. was added 52 mg of sodium borohydride and the mixture was stirred at 0° C. for 15 min. Water was added and the mixture was extracted with ethyl acetate (×3). The combined extracts were dried over magnesium sulphate, filtered and evaporated to leave 504 mg of 5-(3,5-dichlorophenylthio)-4-hydroxymethyl-1-isopropyl-1H-pyrazole-3-carboxylic acid ethyl ester as a colourless oil. Mass spectrum (ES) m/z 389 [M+H]$^+$.

(B) To a solution of 504 mg 5-(3,5-dichlorophenylthio)-4-hydroxymethyl-1-isopropyl-1H-pyrazole-3-carboxylic acid ethyl ester in 5 ml of dichloromethane was added 375 mg of triphenylphosphine and 474 mg of carbon tetrabromide. The reaction mixture was stirred overnight. The solvent was removed and the residue was purified by flash chromatography on silica gel using diethyl ether/iso-hexane for the elution to give 367 mg of 4-bromomethyl-5-(3,5-dichlorophenylthio)-1-isopropyl-1H-pyrazole-3-carboxylic acid ethyl ester as a colourless gum. Mass spectrum (ES) m/z 451 [M+H]$^+$.

To a solution of 55 mg of 4-(hydroxymethyl)pyridine in DMF at 0° C. was added 20 mg sodium hydride (60% in oil). To the mixture was added dropwise a solution of 229 mg of 4-bromomethyl-5-(3,5-dichlorophenylthio)-1-isopropyl-1H-pyrazole-3-carboxylic acid ethyl ester in 2 ml of N,N-dimethylformamide. After 15 min water was added and the mixture was extracted with dichloromethane (×3). The combined extracts were dried over magnesium sulphate, filtered and evaporated. The residue was purified by flash chromatography using ethyl acetate/iso-hexane for the elution to give 80 mg of 5-(3,5-dichlorophenylthio)-1-isopropyl-4-[(4-pyridyl)methyl]-1H-pyrazole-3carboxylic acid ethyl ester as a colourless gum. Mass spectrum (ESI) m/z 480 [M]$^+$.

EXAMPLES 8a

The compound shown in table 5 were prepared in a manner analogous to that described in example 8

TABLE 5

| Example | Structure | MS (ES) (M + H)$^+$ |
|---|---|---|
| 8a | 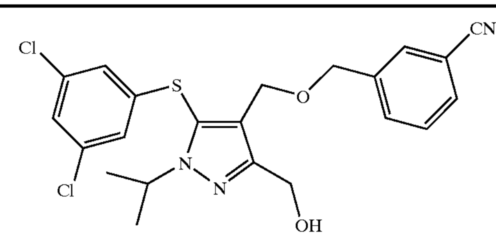 | 462 (M$^+$) |
| 8b | 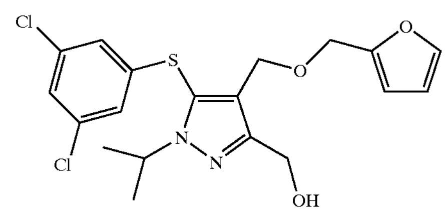 | 427.35 |

EXAMPLE 9

Carbamic acid [5-(3,5-dichlorophenylthio)-1-isopropyl-4-[(4-pyridyl)methoxymethyl]-1H-pyrazol-3-yl]methyl ester To a solution of 120 mg of 5-(3,5-Dichlorophenylthio)-1-isopropyl-4-[(4-pyridyl)methoxymethyl]-1H-pyrazole-3-methanol in 1 ml of dichloromethane at 0° C. was added 11 mg of trichloroacetyl isocyanate. The mixture was stirred for 2 h at 0° C. then the solvent was removed. The residue was dissolved in 2 ml of methanol and 1 ml of water, 100 mg of potassium carbonate added, and the mixture stirred at room temperature for 1 h. The mixture was partitioned between ethyl acetate and water. The combined extracts were dried over magnesium sulphate, filtered and evaporated. The residue was purified by flash chromatography using methanol/dichloromethane for the elution to give 12 mg of carbamic acid [5-(3,5-dichlorophenylthio)-1-isopropyl-4-[(4-pyridyl)methoxymethyl]-1H-pyrazol-3-yl]methyl ester as a white solid. Mass spectrum (ES) m/z 481 [M]+. 1H NMR (DMSO-d6) 1.25 (d, 6H), 4.50 (s, 2H), 4.52 (s, 2H), 4.80 (m, 1H), 5.05 (s, 2H), 6.55 (br s, 1H), 6.75 (br s, 1H), 7.08 (m, 2H), 7.16 (d, 2H) 7.45 (m, 1H), 8.43 (d, 2H).

What is claimed is:

1. A compound according to the formula

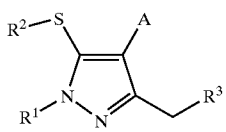

I wherein
- $R^1$ is alkyl or substituted alkyl;
- $R^2$ is aryl or substituted aryl;
- $R^3$ is hydroxy, amino, azido, hydroxy-$C_{1-4}$-alkyl, $C_{1-4}$-alkyl-sulfonyl-amino or a group of the formula —X—C(=O)—Z, wherein X is NR'''', O or a single bond; wherein R'''' is hydrogen or $C_{1-4}$-alkyl, and Z is $C_{1-4}$-alkyl, $C_{1-4}$-alkoxy or NR''R'''; wherein R'', R''' are independently of each other hydrogen or $C_{1-4}$-alkyl;
- A is alkyl, substituted alkyl, aryl-methyl, substituted aryl-methyl, aryl-methoxy-methyl, substituted aryl-methoxy-methyl, heterocyclyl-methyl, substituted heterocyclyl-methyl, heterocyclyl-methoxy-methyl or substituted heterocyclyl-methoxy-methyl;

and the pharmaceutically acceptable salts thereof.

2. The compound according to claim 1 wherein
- $R^1$ is $C_{1-12}$-alkyl or $C_{1-12}$-alkyl substituted with 1–6 fluorines;
- $R^2$ is aryl or aryl substituted with 1–5 substituents selected from $C_{1-4}$-alkyl, $C_{1-4}$-alkoxy, $C_{1-4}$-alkylthio, fluorine, chlorine, bromine and cyano; $C_{1-4}$-alkyl substituted with 1–3 substituents selected from hydroxy, $C_{1-4}$-alkoxy, $CONH_2$ and NRR', wherein R and R' are independently of each other hydrogen, $C_{1-4}$-alkyl or —C(=O)$CH_3$;
- $R^3$ is hydroxy, amino, azido, hydroxy-$C_{1-4}$-alkyl, $C_{1-4}$-alkyl-sulfonyl-amino or a group of the formula —X—C(=O)—Z, wherein X is NR'''', O or a single bond; wherein R'''' is hydrogen or $C_{1-4}$-alkyl, and Z is $C_{1-4}$-alkyl, $C_{1-4}$-alkoxy or NR''R'''; wherein R'', R''' are independently of each other hydrogen or $C_{1-4}$-alkyl;
- A is $C_{1-12}$-alkyl, hydroxy-methyl, aryl-methyl, substituted aryl-methyl wherein the aryl is substituted with 1–5 substituents selected from $C_{1-4}$-alkoxy, fluorine, chlorine and bromine, aryl-methoxy-methyl, substituted aryl-methoxy-methyl wherein the aryl is substituted with 1–5 substituents selected from $C_{1-4}$-alkyl, $C_{1-4}$-alkoxy, $C_{1-4}$-alkylthio, $C_{1-4}$-alkylamino, hydroxy, cyano, amino, mercapto, fluorine, chlorine and bromine, heterocyclyl-methyl, substituted heterocyclyl-methyl wherein the heterocyclyl is substituted with 1–4 substituents selected from $C_{1-4}$-alkyl, $C_{1-4}$-alkoxy, $C_{1-4}$-alkylthio, $C_{1-4}$-alkylamino, hydroxy, cyano, amino, mercapto, fluorine, chlorine and bromine, heterocyclyl-methoxy-methyl or substituted heterocyclyl-methoxy-methyl wherein the heterocyclyl is substituted with 1–4 substituents selected from $C_{1-4}$-alkyl, $C_{1-4}$-alkoxy, $C_{1-4}$-alkylthio, $C_{1-4}$-alkylamino, hydroxy, cyano, amino, mercapto, fluorine, chlorine and bromine.

3. The compound according to claim 1 wherein
- $R^1$ is $C_{1-12}$-alkyl;
- $R^2$ is phenyl or phenyl substituted with 1–5 substituents selected from $C_{1-4}$-alkyl, $C_{1-4}$-alkoxy, $C_{1-4}$-alkylthio, fluorine, chlorine, bromine and cyano;
- $R^3$ is hydroxy, amino, azido, $C_{1-4}$-alkyl-sulfonyl-amino or a group of the formula —X—C(=O)—Z, wherein X is NR'''' or O; wherein R'''' is hydrogen or $C_{1-4}$-alkyl, and Z is $C_{1-4}$-alkyl, $C_{1-4}$-alkoxy or NR''R'''; wherein R'', R''' are independently of each other hydrogen or $C_{1-4}$-alkyl;
- A is heterocyclyl-methyl, substituted heterocyclyl-methyl wherein the heterocyclyl is substituted with 1–4 substituents selected from $C_{1-4}$-alkyl, fluorine, chlorine and bromine or heterocyclyl-methoxy-methyl.

4. The compound according to claim 1 wherein
- $R^1$ is $C_{1-7}$-alkyl;
- $R^2$ is phenyl substituted with 1–5 substituents selected from fluorine, chlorine, bromine and cyano;
- $R^3$ is hydroxy or a group of the formula —X—C(=O)—Z, wherein X is NR'''' or O; wherein R'''' is hydrogen or $C_{1-4}$-alkyl, and Z is NR''R'''; wherein R'', R''' are independently of each other hydrogen or $C_{1-4}$-alkyl;
- A is heterocyclyl-methyl, substituted heterocyclyl-methyl wherein the heterocyclyl is substituted with 1–4 substituents selected from $C_{1-4}$-alkyl, $C_{1-4}$-alkoxy, $C_{1-4}$-alkylthio, $C_{1-4}$-alkylamino, hydroxy, cyano, amino, mercapto, fluorine, chlorine and bromine, or heterocyclyl-methoxy-methyl.

5. The compound according to claim 1 wherein
- $R^1$ is $C_{1-4}$-alkyl;
- $R^2$ is phenyl substituted with 1–3 substituents selected from fluorine, chlorine, bromine and cyano;
- $R^3$ is a group of the formula —X—C(=O)—Z, wherein X is NR'''' or O; wherein R'''' is hydrogen or $C_{1-4}$-alkyl, and Z is NR''R'''; wherein R'', R''' are independently of each other hydrogen or $C_{1-4}$-alkyl;
- A is heterocyclyl-methyl.

6. The compound according to claim 1 wherein
- $R^1$ is iso-propyl;
- $R^2$ is phenyl substituted with 1–3 substituents selected from chlorine and cyano;
- $R^3$ is a group of the formula —X—C(=O)—Z, wherein X is O, and Z is NR''R'''; wherein R'', R''' are independently of each other hydrogen or $C_{1-4}$-alkyl;
- A is pyridyl-methyl.

7. A compound selected from the group consisting of:
5-(3,5-Dichlorophenylthio)-1-isopropyl-4-[(4-pyridyl)methyl]-1H-pyrazole-3-methanol,
Carbamic acid [5-(3,5-dichlorophenylthio)-1-isopropyl-4-[(4-pyridyl)methyl]-1H-pyrazol-3-yl]methyl ester,
Methylcarbamic acid [5-(3,5-dichlorophenylthio)-1-isopropyl-4-[(4-pyridyl)methyl]-1H-pyrazol-3-yl]methyl ester,
5-(3,5-Dichlorophenylthio)-1-isopropyl-4-[(4-pyridyl)methyl]-1H-pyrazole-3-methylamine,
1-[[5-(3,5-Dichlorophenylthio)-1-isopropyl-4-[(4-pyridyl)methyl]-1H-pyrazol-3-yl]methyl]urea,
N-[[5-(3,5-Dichlorophenylthio)-1-isopropyl-4-[(4-pyridyl)methyl]-1H-pyrazol-3-yl]methyl]methanesulfonamide,
Methyl [[5-(3,5-dichlorophenylthio)-1-isopropyl-4-[(4-pyridyl)methyl]-1H-pyrazol-3-yl]methyl]carbomate,
5-(3,5-Dichlorophenylthio)-1-isopropyl-4-[(4-pyridyl)methyl]-1H-pyrazole-3-methanol,
Carbamic acid [5-(3,5-dichlorophenylthio)-1-isopropyl-4-[(4-pyridyl)methoxymethyl]-1H-pyrazol-3-yl]methyl ester, Carbamic acid [5-(3,5-dichlorophenylthio)-1-isopropyl-4-[(4-pyridyl)methyl]-1H-pyrazol-3-yl]methyl ester,
5-(3,5-Dichlorophenylthio)-1-ethyl-4-[(4-pyridyl)methyl]-1H-pyrazole-3-methanol,
5-(3,5-Dichlorophenylthio)-1-isopropyl-4-(2-thenyl)-1H-pyrazole-3-methanol,
5-(3,5-Difluorophenylthio)-1-isopropyl-4-[(4-pyridyl)methyl]-1H-pyrazole-3-methanol,
Carbamic acid [5-(3,5-dichlorophenylthio)-1-isopropyl-4-(2-thenyl)-1H-pyrazol-3-yl]methyl ester,
Carbamic acid [5-(3,5-difluorophenylthio)-1-isopropyl-4-[(4-pyridyl)methyl]-1H-pyrazol-3-yl]methyl ester,
5-(3-Bromo-5-chlorophenylthio)-1-isopropyl-4-[(4-pyridyl)methyl]-1H-pyrazole-3-methanol,
4-[(5-Bromo-2-methyl-4-pyrimidinyl)methyl]-5-(3,5-dichlorophenylthio)-1-isopropyl-1H-pyrazole-3-methanol,
5-(3,5-Dichlorophenylthio)-1-isopropyl-4-(3-methoxybenzyl)-1H-pyrazole-3-methanol,
5-(3,5-Dichlorophenylthio)-4-(3,4-difluorobenzyl)-1-isopropyl-1H-pyrazole-3-methanol,
5-(3,5-Difluorophenylthio)-4-ethyl-1-isopropyl-1H-pyrazole-3-methanol,
Carbamic acid [5-(3,5-dichlorophenylthio)-4-ethyl-1-isopropyl-1H-pyrazol-3-yl]methyl ester,
Carbamic acid [5-(3,5-difluorophenylthio)-4-(hydroxymethyl)-1-isopropyl-1H-pyrazol-3-yl]methyl ester,
3-[[5-(3,5-Dichlorophenylthio)-3-(hydroxymethyl)-1-isopropyl-1H-pyrazol-4-yl]methoxymethyl]benzonitrile,
5-(3,5-Dichlorophenylthio)-4-[(2-furfuryloxy)methyl]-1-isopropyl-1H-pyrazole-3-methanol,
5-(3,5-Dichlorophenylthio)-1-isopropyl-1H-pyrazole-3,4-dimethanol,
Carbamic acid [5-(3,5-dichlorophenylthio)-1-isopropyl-4-(3-methoxybenzyl)-1H-pyrazol-3-yl]methyl ester,
3-Chloro-5-[5-(hydroxymethyl)-2-isopropyl-4-[(4-pyridyl)methyl]-2H-pyrazol-3-ylthio]benzonitrile,
Carbamic acid [5-(3-chloro-5-cyanophenylthio)-1-isopropyl-4-[(4-pyridyl)methyl]-1H-pyrazol-3-yl]methyl ester and
5-(3-Chlorophenylthio)-1-isopropyl-4-[(4-pyridyl)methyl]-1H-pyrazole-3-methanol.

8. A pharmaceutical composition for the treatment of HIV infection comprising a pharmaceutically effective amount of a compound according to claim 1 and a pharmaceutically acceptable inert carrier.

9. A method for the treatment of human immunodeficiency virus (HIV) infection comprising administering to a person infected with HIV a pharmaceutically effective amount of a compound according to claim 1.

* * * * *

UNITED STATES PATENT AND TRADEMARK OFFICE
CERTIFICATE OF CORRECTION

PATENT NO. : 6,538,015 B1　　　　　　　　　　　　　　　　　　　　　　　　　　　Page 1 of 1
DATED : March 25, 2003
INVENTOR(S) : Brian W. Dymock et al.

It is certified that error appears in the above-identified patent and that said Letters Patent is hereby corrected as shown below:

Column 52,
Line 64, insert -- methoxy -- before "methyl" at beginning of sentence.

Column 53,
Line 1, delete "dichlorophenylthio" and insert therefor -- dicyanophenylthio --

Signed and Sealed this

Fifth Day of August, 2003

JAMES E. ROGAN
*Director of the United States Patent and Trademark Office*